(12) United States Patent
Bergmann

(10) Patent No.: US 12,399,186 B2
(45) Date of Patent: *Aug. 26, 2025

(54) METHOD FOR DIAGNOSING OR MONITORING KIDNEY FUNCTION OR DIAGNOSING KIDNEY DYSFUNCTION

(71) Applicant: SPHINGOTEC GMBH, Henningsdorf (DE)

(72) Inventor: Andreas Bergmann, Berlin (DE)

(73) Assignee: SPHINGOTEC GMBH, Henningsdorf (DE)

( * ) Notice: Subject to any disclaimer, the term of this patent is extended or adjusted under 35 U.S.C. 154(b) by 46 days.

This patent is subject to a terminal disclaimer.

(21) Appl. No.: 17/328,100

(22) Filed: May 24, 2021

(65) Prior Publication Data
US 2021/0333292 A1 Oct. 28, 2021

Related U.S. Application Data

(63) Continuation of application No. 16/173,236, filed on Oct. 29, 2018, now Pat. No. 11,016,107, which is a continuation of application No. 15/590,571, filed on May 9, 2017, now Pat. No. 10,114,029, which is a continuation of application No. 14/432,957, filed as application No. PCT/EP2013/070470 on Oct. 1, 2013, now Pat. No. 9,664,695.

(30) Foreign Application Priority Data

Oct. 2, 2012 (EP) .................................... 12187051
Jun. 3, 2013 (EP) .................................... 13170327

(51) Int. Cl.
*G01N 33/74* (2006.01)
*G01N 33/543* (2006.01)
*G01N 33/68* (2006.01)

(52) U.S. Cl.
CPC ....... *G01N 33/74* (2013.01); *G01N 33/54366* (2013.01); *G01N 33/6893* (2013.01); *G01N 2333/70* (2013.01); *G01N 2800/347* (2013.01); *G01N 2800/52* (2013.01)

(58) Field of Classification Search
CPC ............. G01N 33/74; G01N 33/54366; G01N 33/6893; G01N 2333/70; G01N 2800/347; G01N 2800/52
See application file for complete search history.

(56) References Cited

U.S. PATENT DOCUMENTS

| | | | |
|---|---|---|---|
| 8,013,123 B2 | 9/2011 | Bergmann et al. |
| 8,501,418 B2 | 8/2013 | Kas et al. |
| 2008/0261232 A1 | 10/2008 | Bergmann et al. |
| 2012/0034240 A1 | 2/2012 | Kas et al. |
| 2013/0129750 A1 | 5/2013 | Kas et al. |

FOREIGN PATENT DOCUMENTS

| | | |
|---|---|---|
| EP | 2293079 A2 | 3/2011 |
| WO | 2012017071 A1 | 2/2012 |

OTHER PUBLICATIONS

Freitas (Clinics 2008 64:483). (Year: 2008).*
International Search Report for PCT/EP2013/070470 dated Apr. 12, 2013.
Zoccali, C. et al., "Plasma met-enkephalin and leu-enkephalin in chronic renal failure," Nephrology, Dialysis, Transplantation: Official Publication of the European Dialysis and Transplant Association 1987, vol. 1, No. 4, pp. 219-222.
Smith, R. et al., "Studies on Circulating Met-Enkephalin and Beta-endorphin: Normal Subjects and Patients with Renal and Adrenal Disease," Clinical Endocrinology, Jan. 1, 1981, vol. 15, No. 3, pp. 291-300.
Smith, R. et al., "Effect of liver and renal dysfunction on circulating methionine-enkephalin immunoreactivity," Neuroscience Letters, Oct. 10, 1985, vol. 60, No. 3, pp. 301-305.
Doehner, W. et al., "Elevated Plasma Levels of Neuropeptide Proenkephalin A Predict Mortality and Functional Outcome in Ischemic Stroke," Journal of the American College of Cardiology, Apr. 16, 2012, vol. 60, No. 4, pp. 346-354.

* cited by examiner

*Primary Examiner* — Changhwa J Cheu
(74) *Attorney, Agent, or Firm* — Ryan Pool

(57) ABSTRACT

A method for (a) diagnosing or monitoring kidney function in subject or (b) diagnosing kidney dysfunction in a subject or (c) predicting or monitoring the risk of an adverse events in a diseased subject or (d) predicting or monitoring the success of a therapy or intervention comprising
determining the level of Pro-Enkephalin (PENK) or fragments thereof of at least 5 amino acids in a bodily fluid obtained from said subject; and correlating said level of Pro-Enkephalin or fragments thereof with
(a) kidney function in a subject or
(b) kidney dysfunction in said subject or
(c) enhanced risk of adverse events or
(d) success of a therapy or intervention in a diseased subject.

Figure 1:
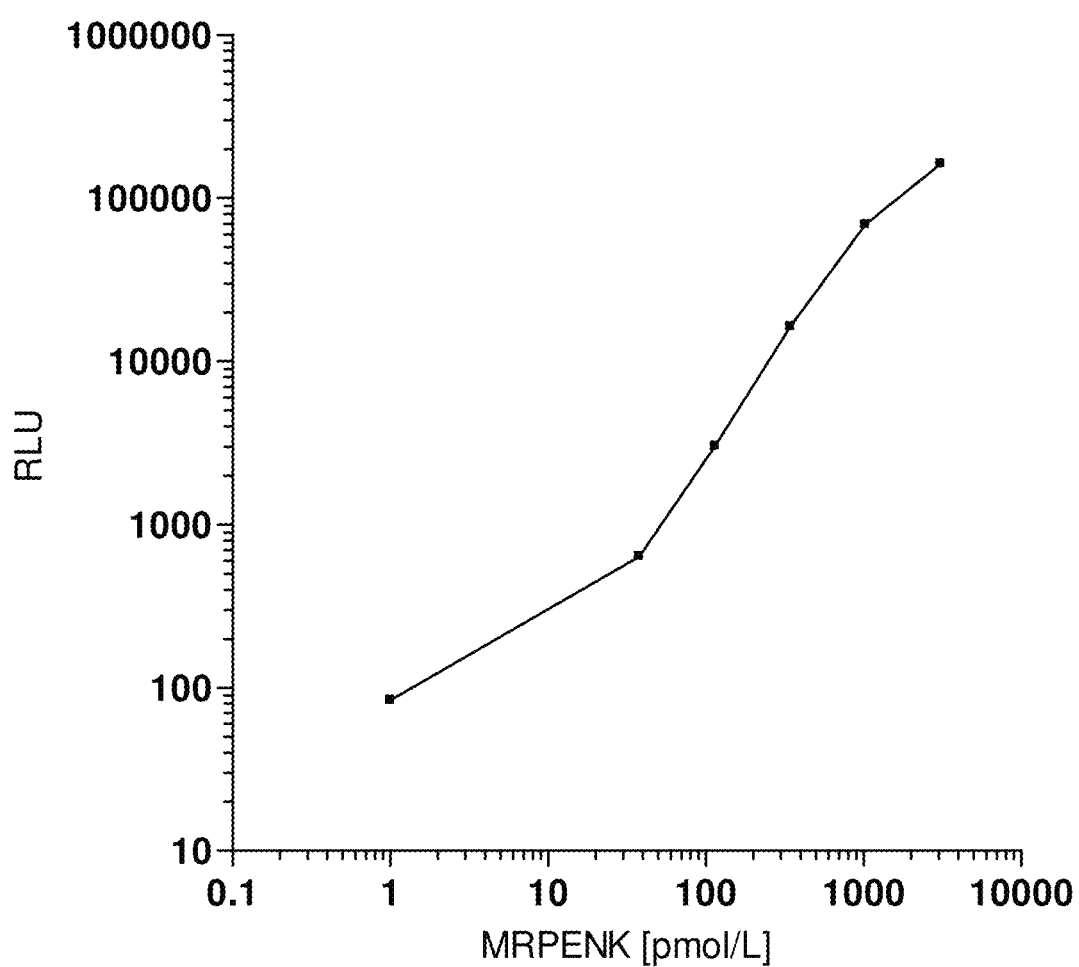

57 Claims, 20 Drawing Sheets
Specification includes a Sequence Listing.

Predicting in-hospital mortality

Results from logistic regression:

| Model | N | Events | Model Chi2 | d.f. | LR p-value | C index [95-CI] |
|---|---|---|---|---|---|---|
| crea.clearance | 98 | 24 | 4.02 | 1 | 0.04485 | 0.638 [0.503,0.772] |
| PENK | 101 | 27 | 17.53 | 1 | 0.00003 | 0.744 [0.631,0.859] |
| APACHE | 101 | 27 | 19.98 | 1 | 0.00001 | 0.783 [0.681,0.886] |

Predicting in-hospital mortality

- PENK is independent from Apache and provides additional prognostic information:

|  | LR $\chi^2$ | d.f. | p value |
  |---|---|---|---|
  | adding APACHE (Apache) to PENK | 7.07 | 1 | 0.0078 |
  | adding PENK (PENK) to APACHE | 4.62 | 1 | 0.0316 |

- AUC(PENK plus APACHE): 0.794 (vs. 0.783 for APACHE alone)

- Chi$^2$: 26.4 (vs. 20.0 for APACHE)

Fig. 10:

Predicting in-hospital mortality

Results from logistic regression:

| Model | N | Events | Model Chi2 | d.f. | LR p-value | C index [95-CI] |
|---|---|---|---|---|---|---|
| crea.clearance | 58 | 11 | 5.26 | 1 | 0.02188 | 0.721 [0.528,0.913] |
| PENK | 60 | 13 | 18.9 | 1 | 0.00001 | 0.849 [0.724,0.979] |
| APACHE | 60 | 13 | 20.10 | 1 | 0.00001 | 0.837 [0.693,0.981] |

Predicting in-hospital mortality

- PENK is independent from Apache and provides additional prognostic information:

| | LR $\chi^2$ | d.f. | p value |
|---|---|---|---|
| adding APACHE (Apache) to PENK | 7.69 | 1 | 0.0056 |
| adding PENK (PENK) to APACHE | 6.4 | 1 | 0.0114 |

- AUC(PENK plus APACHE): 0.890 (vs. 0.837 for APACHE alone)

- Chi$^2$: 26.6 (vs. 20.2 for APACHE)

Predicting in-hospital mortality

☐ PENK is independent from Creatinine Clearance and provides superior prognostic information:

|  | LR χ² | d.f. | p value |
|---|---|---|---|
| adding crea.clearance (crea.clearance) to PENK | 3.31 | 1 | 0.069 |
| adding PENK (PENK) to crea.clearance | 18.23 | 1 | <0.0001 |

☐ AUC(PENK plus Crea Cl): 0.913 (vs. 0.851 for PENK alone)

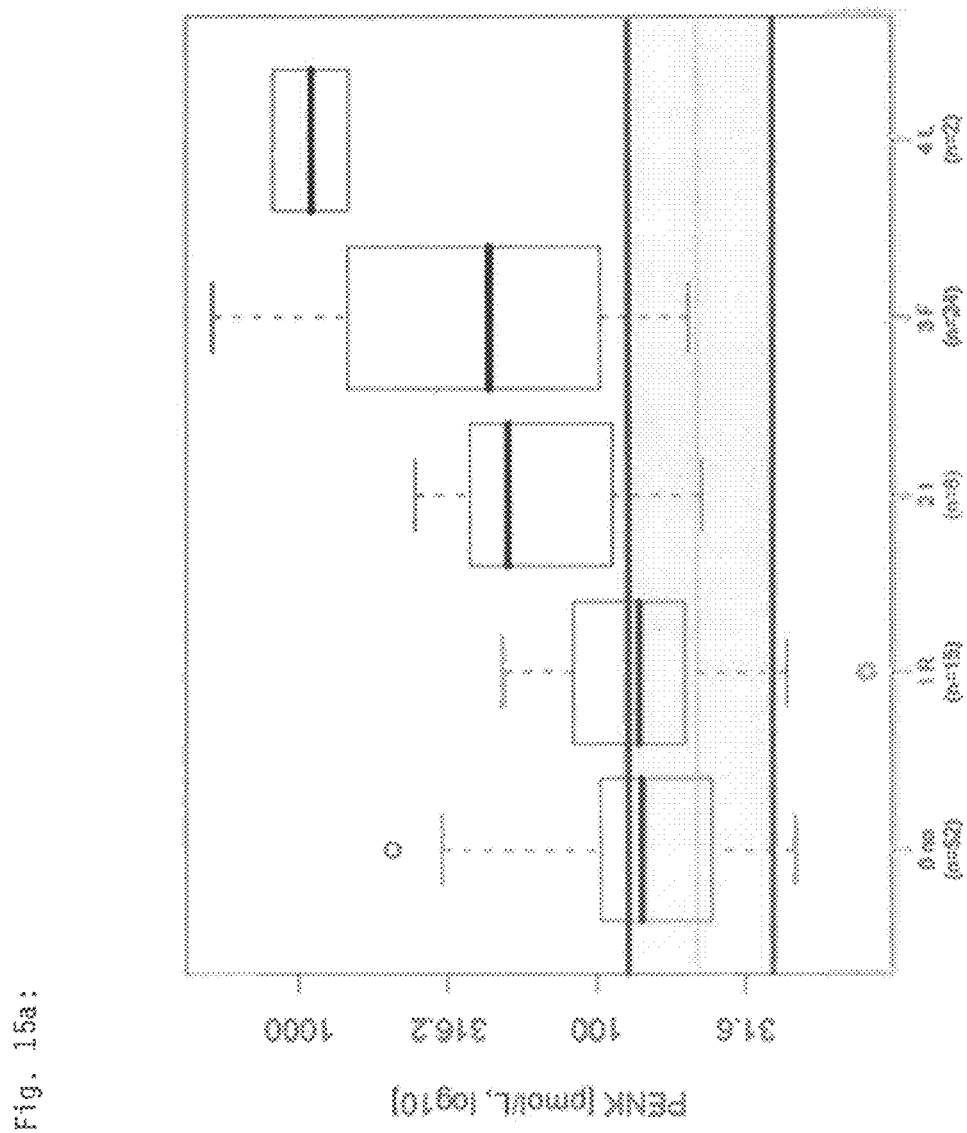

METHOD FOR DIAGNOSING OR MONITORING KIDNEY FUNCTION OR DIAGNOSING KIDNEY DYSFUNCTION

This application is a continuation of U.S. application Ser. No. 16/173,236 filed Oct. 29, 2018, Ser. No. 15/590,571, which is a continuation of U.S. Application No. filed May 9, 2017, which is a continuation of U.S. application Ser. No. 14/432,957, filed Apr. 1, 2015 (now U.S. Pat. No. 9,664, 695), the specifications of which are hereby incorporated by reference herein in their entirety and for which priority is claimed herein.

SEQUENCE LISTING

The instant application contains a Sequence Listing which has been submitted electronically in ASCII format and is hereby incorporated by reference in its entirety. Said ASCII copy, created on Mar. 11, 2025, is named B75021WOUS-CON-A-CON SEQ PROT_ST25.txt and is 7,604 bytes in size.

Subject matter of the present invention is a method for (a) diagnosing or monitoring kidney function in subject or (b) diagnosing kidney dysfunction in a subject or (c) predicting or monitoring the risk of an adverse events in a diseased subject wherein said adverse event is selected from the group comprising worsening of kidney dysfunction including kidney failure, loss of kidney function and end-stage kidney disease or death due to kidney dysfunction including kidney failure, loss of kidney function and end-stage kidney disease or (d) predicting or monitoring the success of a therapy or intervention comprising determining the level of Pro-Enkephalin (PENK) or fragments thereof of at least 5 amino acids in a bodily fluid obtained from said subject; and
  (a) correlating said level of Pro-Enkephalin or fragments thereof with kidney function in a subject or
  (b) correlating said level of Pro-Enkephalin or fragments thereof with kidney dysfunction wherein an elevated level above a certain threshold is predictive or diagnostic for kidney dysfunction in said subject or
  (c) correlating said level of Pro-Enkephalin or fragments thereof with said risk of an adverse event in a diseased subject, wherein an elevated level above a certain threshold is predictive for an enhanced risk of said adverse events or
  (d) correlating said level of Pro-Enkephalin or fragments thereof with success of a therapy or intervention in a diseased subject, wherein a level below a certain threshold is predictive for a success of therapy or intervention.

Met-Enkephalin, a 5 amino acid peptide derived from the Enkephalin precursor (Pre-Pro-Enkephalin), also named "Opioid Growth Factor" (OGF) is released together with Pro-Enkephalin-fragments. The mature peptide binds to different opioid receptors (Koneru et al., 2009). Enkephalin (OGF) was found to have a number of physiological functions. In the CNS it down regulates Substance P associated pain signalling, it plays roles as cytokine (Plotnikoff et al, 1997). Pro-Enkephalin related peptides exhibiting antibiotic actions (Goumon et al., 1998). Pro-Enkephalin and Enkephalin exhibits anti tumor action and acting as pro-apoptotic agents (Tavish et al., 2007, Donahue et al., 2011, Zagon et al., 2009). Enkephalin was reported to be elevated in kidney dysfunction (Smith et al, 1985, Zoccali et al., 1987, Smith et al., 1981). Enkephalin is produced as the larger Pro-Enkephalin and converted by proteolysis to the mature pentapeptides. During maturation process a number of Pro-Enkephalin fragments are generated, which are co-released together with Enkephalin (Ernst et al., 2006).

Subject matter of the present invention is the use of Pro-Enkephalin (PENK) or fragments thereof as marker for kidney function and dysfunction and its clinical utility in healthy and diseased subjects. Subject matter of the present invention is a method for diagnosing or monitoring kidney function in subject or diagnosing kidney dysfunction in a subject or predicting the risk of death or adverse events in a diseased subject.

A subject of the present invention was also the provision of the prognostic and diagnostic power of PENK or fragments thereof for the diagnosis of kidney function, dysfunction and the prognostic value in diseased subjects.

Surprisingly, it has been shown that PENK or fragments are powerful and highly significant biomarker for kidney, its function, dysfunction, risk of death or adverse events and prognosis and monitoring success of therapy or intervention.

Subject matter of the present invention is method for (a) diagnosing or monitoring kidney function in subject or (b) diagnosing kidney dysfunction in a subject or (c) predicting or monitoring the risk of an adverse events in a diseased subject wherein said adverse event is selected from the group comprising worsening of kidney dysfunction including kidney failure, loss of kidney function and end-stage kidney disease or death due to kidney dysfunction including kidney failure, loss of kidney function and end-stage kidney disease or (d) predicting or monitoring the success of a therapy or intervention comprising determining the level of Pro-Enkephalin (PENK) or fragments thereof of at least 5 amino acids in a bodily fluid obtained from said subject; and
  (a) correlating said level of Pro-Enkephalin or fragments thereof with kidney function in a subject or
  (b) correlating said level of Pro-Enkephalin or fragments thereof with kidney dysfunction wherein an elevated level above a certain threshold is predictive or diagnostic for kidney dysfunction in said subject or
  (c) correlating said level of Pro-Enkephalin or fragments thereof with said risk of an adverse event in a diseased subject, wherein an elevated level above a certain threshold is predictive for an enhanced risk of said adverse events or
  (d) correlating said level of Pro-Enkephalin or fragments thereof with success of a therapy or intervention in a diseased subject, wherein a level below a certain threshold is predictive for a success of therapy or intervention.

According to the present invention said Pro-Enkephalin or fragments thereof is not leu-enkephalin and not met-enkephalin in one specific embodiment. In another specific embodiment said Pro-Enkephalin fragment is MR-Pro-Enkephalin (MRPENK) or a fragment thereof having at least 5 amino acids.

To put it in other words: Subject matter of the present invention is method for (a) diagnosing or monitoring kidney function in subject or (b) diagnosing kidney dysfunction in a subject or (c) predicting or monitoring the risk of an adverse events in a diseased subject wherein said adverse event is selected from the group comprising worsening of kidney dysfunction including kidney failure, loss of kidney function and end-stage kidney disease or death due to kidney dysfunction including kidney failure, loss of kidney function and end-stage kidney disease or (d) predicting or monitoring the success of a therapy or intervention comprising
    determining the level of immunoreactive analyte by using at least one binder that binds to a region within the amino acid sequence of Pro-Enkephalin (PENK) in a bodily fluid obtained from said subject; and
    (a) correlating said level of immunoreactive analyte with kidney function in a subject or
    (b) correlating said level of immunoreactive analyte with kidney dysfunction wherein an elevated level above a certain threshold is predictive or diagnostic for kidney dysfunction in said subject or
    (c) correlating said level of immunoreactive analyte with said risk of an adverse event in a diseased subject, wherein an elevated level above a certain threshold is predictive for an enhanced risk of said adverse events or
    (d) correlating said level of immunoreactive analyte with success of a therapy or intervention in a diseased subject, wherein a level below a certain threshold is predictive for a success of therapy or intervention.

According to the present invention said immunoreactive analyte is not leu-enkephalin and not met-enkephalin in a specific embodiment. In another specific embodiment said immunoreactive analyte is MR-Pro-Enkephalin (MRPENK) or a fragment thereof having at least 5 amino acids.

This means in case a binder is used in the methods of the present invention that binds to a region within the amino acid sequence of Pro-Enkephalin (PENK) in a bodily fluid then the terms "determining the level of Pro-Enkephalin (PENK) or fragments thereof of at least 5 amino acids in a bodily fluid obtained from said subject" are equivalent to "determining the level of immunoreactive analyte by using at least one binder that binds to a region within the amino acid sequence of Pro-Enkephalin (PENK) in a bodily fluid obtained from said subject". In a specific embodiment a binder is used in the methods of the present invention that binds to a region within the amino acid sequence of Pro-Enkephalin (PENK) in a bodily fluid. In a specific embodiment said binder used in the methods of the present invention does not bind to a region within the amino acid sequence of leu-enkephalin or met-enkephalin in a bodily fluid. In another specific embodiment of the present invention said at least one binder binds to MR-Pro-Enkephalin (MRPENK) or a fragment thereof having at least 5 amino acids.

The term "subject" as used herein refers to a living human or non-human organism. Preferably herein the subject is a human subject. The subject may be healthy or diseased if not stated otherwise. In one embodiment of the invention said subject has not suffered a stroke. In another embodiment said subject is not an acute stroke patient.

The term "elevated level" means a level above a certain threshold level. The term "elevated" level may mean a level above a value that is regarded as being a reference level.

Predicting or monitoring the success of a therapy or intervention may be e.g. the prediction or monitoring of success of renal replacement therapy using measurement of Pro-Enkephalin (PENK) or fragments thereof of at least 5 amino acids.

Predicting or monitoring the success of a therapy or intervention may be e.g. the prediction or monitoring of success of treatment with hyaluronic acid in patients having received renal replacement therapy using measurement of Pro-Enkephalin (PENK) or fragments thereof of at least 5 amino acids.

Predicting or monitoring the success of a therapy or intervention may be e.g. the prediction or monitoring recovery of renal function in patients with impaired renal function prior to and after renal replacement therapy and/or pharmaceutical interventions using measurement of PENK or fragments thereof of at least 5 amino acids.

A bodily fluid may be selected from the group comprising blood, serum, plasma, urine, cerebro spinal liquid (csf), and saliva.

Determination of Pro-Enkephalin or fragments thereof exhibit kidney function in a subject. An increased concentration of Pro-Enkephalin or fragments thereof indicates a reduced kidney function. During follow up measurements, a relative change of Pro-Enkephalin or fragments thereof correlates with the improvement (lowering Pro-Enkephalin or fragments thereof) and with the worsening (increased Pro-Enkephalin or fragments thereof) of the subjects kidney function.

Pro-Enkephalin or fragments thereof are diagnostic for kidney dysfunction wherein an elevated level above a certain threshold is predictive or diagnostic for kidney dysfunction in said subject.

During follow up measurements, a relative change of Pro-Enkephalin or fragments thereof correlates with the improvement (lowering Pro-Enkephalin or fragments thereof) and with the worsening (increased Pro-Enkephalin or fragments thereof) of the subjects kidney dysfunction.

Pro-Enkephalin or fragments thereof are superior in comparison to other markers for kidney function/dysfunction diagnosis and follow up (NGAL, blood creatinine, creatinine clearance, Cystatin C, Urea). Superiority means higher specificity, higher sensitivity and better correlation to clinical endpoints.

Correlating said level of Pro-Enkephalin or fragments thereof with a risk of death or an adverse event in a diseased subject, wherein an elevated level above a certain threshold is predictive for an enhanced risk of death or adverse events. Also in this aspect, Pro-Enkephalin or fragments thereof are superior to above mentioned clinical markers.

Risk according to the present invention correlates with the risk as defined by the RIFLE criteria, Venkataramaran and Kellum, 2006).

The diseased person may suffer from a disease selected from chronical kidney failure caused by immune responses to inflammation, acute kidney failure caused by decreased blood flow which may occur with extremely low blood pressure caused by trauma, traumatic patients, surgery, stroke, acute and chronic renal failure, patients with SIRS, Sepsis, Septic Shock, Stroke, acute- and post Myocardial Infarction, acute- and chronic Heart Failure, local and systemic bacterial and viral infections, autoimmune diseases, burned patients, cancer, liver diseases, lung diseases, patients receiving nephrotoxins such as cyclosporine, antibiotics including aminoglycosides and anticancer drugs such as cisplatin.

The therapy or intervention supporting or replacing kidney function may comprise various methods of renal replacement therapy including but not limited to hemodialysis, peritoneal dialysis, hemofiltration and renal transplantation.

An adverse event may be selected from the group comprising worsening of kidney dysfunction including kidney failure, loss of kidney function and end-stage kidney disease (according to the RIFLE criteria, Venkatamaran and Kellum, 2006).

In one embodiment of the invention it should be understood that the term fragments of Pro-Enkephalin also include Leu-Enkephalin and Met-Enkephalin.

Subject matter according to the present invention is a method wherein the level of Pro-Enkephalin or fragments thereof of at least 5 amino acids is determined by using a binder, at least one binder, to Pro-Enkephalin or fragments thereof of at least 5 amino acids. In one embodiment of the invention said binder is selected from the group comprising an antibody, an antibody fragment or a non-Ig-Scaffold binding to Pro-Enkephalin or fragments thereof of at least 5 amino acids. In a specific embodiment said at least one binder binds to a region with the sequences selected from the group comprising SEQ ID No. 1, 2, 3, 4, 5, 6, 7, 8, 9 and 10. In a specific embodiment said binder do not bind to enkephalin peptides [Met]enkephalin SEQ ID No:3, and [Leu] enkephalin. SEQ ID No:4. In a specific embodiment said at least one binder binds to a region with the sequences selected from the group comprising SEQ ID No. 1, 2, 5, 6, 7, 8, 9 and 10. In another specific embodiment said at least one binder binds to a region with the sequences selected from the group comprising SEQ ID No. 2, 5, 6, and 10. In another very specific embodiment said binder bind to Pro-Enkephalin 119-159, Mid regional Pro-Enkephalin-fragment, MRPENK.

Pro-Enkephalin has the following sequence:

```
(Pro-Enkephalin (1-243)
                                      SEQ ID NO. 1
ECSQDCATCSYRLVRPADINFLACVMECEGKLPSLKIWETCKELLQLSKP

ELPQDGTSTL

RENSKPEESHLLAKRYGGFMKRYGGFMKKMDELYPMEPEEEANGSEILAK

RYGGFMKKDAEEDDSLANSSDLLKELLETGDNRERSHHQDGSDNEEEVSK

RYGGFMRGLKRSPQLEDEAKELQKRYGGFMRRVGRPEWWMDYQKRYGGFL

KRFAEALPSDEEGESYSKEVPEMEKRYGGF MRF
```

Fragments of Pro-Enkephalin that may be determined in a bodily fluid may be e.g. selected from the group of the following fragments:

```
SEQ ID NO. 2 (Synenkephalin, Pro-Enkephalin 1-73)
ECSQDCATCSYRLVRPADINFLACVMECEGKLPSLKIWETCKELLQLSKP

ELPQDGTSTL

RENSKPEESHLLA

SEQ ID NO. 3 (Met-Enkephalin)
YGGFM

SEQ ID NO. 4 (Leu-Enkephalin)
YGGFL

SEQ ID NO. 5 (Pro-Enkephalin 90-109)
MDELYPMEPEEEANGSEILA

SEQ ID NO 6: (Pro-Enkephalin 119-159, Mid regional
Pro-Enkephalin-fragment, MRPENK)
DAEEDDSLANSSDLLKELLETGDNRERSHHQDGSDNEEEVS SEQ ID NO. 7 (Met-Enkephalin-Arg-Gly-Leu)
YGGFMRGL SEQ ID NO. 8 (Pro-Enkephalin 172-183)
SPQLEDEAKELQ SEQ ID NO. 9 (Pro-Enkephalin 193-203)
VGRPEWWMDYQ SEQ ID NO. 10 (Pro-Enkephalin 213-234)
FAEALPSDEEGESYSKEVPEME SEQ ID NO. 11 (Pro-Enkephalin 213-241)
FAEALPSDEEGESYSKEVPEMEKRYGGF M SEQ ID NO. 12 (Met-Enkephalin-Arg-Phe)
YGGFMRF
```

Determining the level of Pro-Enkephalin including Leu-Enkephalin and Met-Enkephalin or fragments thereof may mean that the immunoreactivity towards Pro-Enkephalin or fragments thereof including Leu-Enkephalin and Met-Enkephalin is determined. A binder used for determination of Pro-Enkephalin including Leu-Enkephalin and Met-Enkephalin or fragments thereof depending of the region of binding may bind to more than one of the above displayed molecules. This is clear to a person skilled in the art.

Thus, according to the present invention the level of immunoreactive analyte by using at least one binder that binds to a region within the amino acid sequence of any of the above peptide and peptide fragments, (i.e. Pro-Enkephalin (PENK) and fragments according to any of the sequences 1 to 12), is determined in a bodily fluid obtained from said subject; and correlated to the specific embodiments of clinical relevance.

In a more specific embodiment of the method according to the present invention the level of MRPENK is determined (SEQ ID NO. 6: Pro-Enkephalin 119-159, Mid regional Pro-Enkephalin-fragment, MRPENK). In a more specific embodiment the level of immunoreactive analyte by using at least one binder that binds to MR-PENK is determined and is correlated to the above mentioned embodiments according to the invention to the specific embodiments of clinical relevance, e.g.

correlating said level of immunoreactive analyte with kidney function in a subject or
  (b) correlating said level of immunoreactive analyte with kidney dysfunction wherein an elevated level above a certain threshold is predictive or diagnostic for kidney dysfunction in said subject or
  (c) correlating said level of immunoreactive analyte with said risk of an adverse event in a diseased subject, wherein an elevated level above a certain threshold is predictive for an enhanced risk of said adverse events or
  (d) correlating said level of immunoreactive analyte with success of a therapy or intervention in a diseased subject, wherein a level below a certain threshold is predictive for a success of therapy or intervention.

Alternatively the level of any of the above analytes may be determined by other nalytical methods e.g. mass spectroscopy.

Thus, subject matter of the present invention is method for (a) diagnosing or monitoring kidney function in subject or (b) diagnosing kidney dysfunction in a subject or (c) predicting or monitoring the risk of an adverse events in a diseased subject wherein said adverse event is selected from the group comprising worsening of kidney dysfunction including kidney failure, loss of kidney function and end-stage kidney disease or death due to kidney dysfunction including kidney failure, loss of kidney function and end-stage kidney disease or (d) predicting or monitoring the success of a therapy or intervention comprising determining the level of immunoreactive analyte by using at least one binder that binds to a region within the amino acid sequence of a peptide selected from the group comprising the peptides and fragments of SEQ ID No. 1 to 12 in a bodily fluid obtained from said subject; and
(a) correlating said level of Pro-Enkephalin or fragments thereof with kidney function in a subject or
(b) correlating said level of Pro-Enkephalin or fragments thereof with kidney dysfunction wherein an elevated level above a certain threshold is predictive or diagnostic for kidney dysfunction in said subject or
(c) correlating said level of Pro-Enkephalin or fragments thereof with said risk of an adverse event in a diseased subject, wherein an elevated level above a certain threshold is predictive for an enhanced risk of said adverse events or
(d) correlating said level of Pro-Enkephalin or fragments thereof with success of a therapy or intervention in a diseased subject, wherein a level below a certain threshold is predictive for a success of therapy or intervention.

In a specific embodiment the level of immunoreactive analyte is determined by using at least one binder that binds to a region within the amino acid sequence of a peptide selected from the group comprising Pro-Enkephalin or fragments thereof of at least 5 amino acids. In a specific embodiment said at least one binder binds to a region with the sequences selected from the group comprising SEQ ID No. 1, 2, 3, 4, 5, 6, 7, 8, 9 and 10. In a specific embodiment said binder do not bind to enkephalin peptides [Met]enkephalin SEQ ID No:3, and [Leu]enkephalin. SEQ ID No:4. In a specific embodiment said at least one binder binds to a region with the sequences selected from the group comprising SEQ ID No. 1, 2, 5, 6, 7, 8, 9 and 10. In another specific embodiment said at least one binder binds to a region with the sequences selected from the group comprising SEQ ID No. 2, 5, 6, and 10. In another very specific embodiment said binder binds to Pro-Enkephalin 119-159, Mid regional Pro-Enkephalin-fragment, MRPENK. The before mentioned binder binds to said peptides in a bodily fluid obtained from said subject.

In one embodiment of the invention said binder is selected from the group comprising an antibody, an antibody fragment or a non-Ig-Scaffold binding to Pro-Enkephalin or fragments thereof of at least 5 amino acids.

In a more specific embodiment the level of immunoreactive analyte by using at least one binder that binds to a region within the amino acid sequence of Pro-Enkephalin 119-159, Mid regional Pro-Enkephalin-fragment, MRPENK (SEQ ID No. 6) in a bodily fluid obtained from said subject.

In a specific embodiment the level of Pro-Enkephalin or fragments thereof are measured with an immunoassay using antibodies or fragments of antibodies binding to Pro-Enkephalin or fragments thereof. An immunoassay that may be useful for determining the level of Pro-Enkephalin or fragments thereof of at least 5 amino acids may comprise the steps as outlined in Example 1. All thresholds and values have to be seen in correlation to the test and the calibration used according to Example 1. A person skilled in the art may know that the absolute value of a threshold might be influenced by the calibration used. This means that all values and thresholds given herein are to be understood in context of the calibration used in herein (Example 1).

According to the invention the diagnostic binder to Pro-Enkephalin is selected from the group consisting of antibodies e.g. IgG, a typical full-length immunoglobulin, or antibody fragments containing at least the F-variable domain of heavy and/or light chain as e.g. chemically coupled antibodies (fragment antigen binding) including but not limited to Fab-fragments including Fab minibodies, single chain Fab antibody, monovalent Fab antibody with epitope tags, e.g. Fab-V5Sx2; bivalent Fab (mini-antibody) dimerized with the CH3 domain; bivalent Fab or multivalent Fab, e.g. formed via multimerization with the aid of a heterologous domain, e.g. via dimerization of dHLX domains, e.g. Fab-dHLX-FSx2; F(ab')2-fragments, scFv-fragments, multimerized multivalent or/and multispecific scFv-fragments, bivalent and/or bispecific diabodies, BITE® (bispecific T-cell engager), trifunctional antibodies, polyvalent antibodies, e.g. from a different class than G; single-domain antibodies, e.g. nanobodies derived from camelid or fish immunoglobulines.

In a specific embodiment the level of Pro-Enkephalin or fragments thereof are measured with an assay using binders selected from the group comprising aptamers, non-Ig scaffolds as described in greater detail below binding to Pro-Enkephalin or fragments thereof.

Binder that may be used for determining the level of Pro-Enkephalin or fragments thereof exhibit an affinity constant to Pro-Enkephalin of at least $10^7$ $M^{-1}$, preferred $10^8$ $M^{-1}$, preferred affinity constant is greater than $10^9$ $M^{-1}$, most preferred greater than $10^{10}$ $M^{-1}$. A person skilled in the art knows that it may be considered to compensate lower affinity by applying a higher dose of compounds and this measure would not lead out-of-the-scope of the invention. Binding affinity may be determined using the Biacore method, offered as service analysis e.g. at Biaffin, Kassel, Germany (http://www.biaffin.com/de/).

A human Pro-Enkephalin-control sample is available by ICI-Diagnostics, Berlin, Germany http://www.ici-diagnostics.com/. The assay may also be calibrated by synthetic (for our experiments we used synthetic MRPENK, SEQ ID NO. 6) or recombinant Pro-Enkephalin or fragments thereof.

In addition to antibodies other biopolymer scaffolds are well known in the art to complex a target molecule and have been used for the generation of highly target specific biopolymers. Examples are aptamers, spiegelmers, anticalins and conotoxins. Non-Ig scaffolds may be protein scaffolds and may be used as antibody mimics as they are capable to bind to ligands or antigenes. Non-Ig scaffolds may be selected from the group comprising tetranectin-based non-Ig scaffolds (e.g. described in US 2010/0028995), fibronectin scaffolds (e.g. described in EP 1266 025; lipocalin-based scaffolds (e.g. described in WO 2011/154420); ubiquitin scaffolds (e.g. described in WO 2011/073214), transferring scaffolds (e.g. described in US 2004/0023334), protein A scaffolds (e.g. described in EP 2231860), ankyrin repeat based scaffolds (e.g. described in WO 2010/060748), microproteins preferably microproteins forming a cystine knot) scaffolds (e.g. described in EP 2314308), Fyn SH3 domain based scaffolds (e.g. described in WO 2011/023685) EGFR-A-domain based scaffolds (e.g. described in WO 2005/040229) and Kunitz domain based scaffolds (e.g. described in EP 1941867).

The threshold for diagnosing kidney disease/dysfunction or for determining the risk of death or an adverse event may be the upper normal range (99 percentile, 80 pmol MRPENK/L, more preferred 100 pmol/L more preferred 120 pmol/L.) A threshold range is useful between 75 and 130 pmol MRPENK/L.

In one specific embodiment the level of Pro Enkephalin is measured with an immunoassay and said binder is an antibody, or an antibody fragment binding to Pro-Enkephalin or fragments thereof of at least 5 amino acids.

In one specific embodiment the assay used comprises two binders that bind to two different regions within the region of Pro-Enkephalin that is aminoacid 133-140 (LKELLETG, SEQ ID No. 13) and aminoacid 152-159 (SDNEEEVS, SEQ ID NO. 14) wherein each of said regions comprises at least 4 or 5 amino acids.

In one embodiment of the assays for determining Pro-Enkephalin or Pro-Enkephalin fragments in a sample according to the present invention the assay sensitivity of said assay is able to quantify the Pro-Enkephalin or Pro-Enkephalin fragments of healthy subjects and is <15 pmol/L, preferably <10 pmol/L and more preferably L<6 pmol/L.

Subject matter of the present invention is the use of at least one binder that binds to a region within the amino acid sequence of a peptide selected from the group comprising the peptides and fragments of SEQ ID No. 1 to 12 in a bodily fluid obtained from said subject in a method a for (a) diagnosing or monitoring kidney function in subject or (b) diagnosing kidney dysfunction in a subject or (c) predicting or monitoring the risk of an adverse events in a diseased subject wherein said adverse event is selected from the group comprising worsening of kidney dysfunction including kidney failure, loss of kidney function and end-stage kidney disease or death due to kidney dysfunction including kidney failure, loss of kidney function and end-stage kidney disease or (d) predicting or monitoring the success of a therapy or intervention. In one embodiment of the invention said binder is selected from the group comprising an antibody, an antibody fragment or a non-Ig-Scaffold binding to Pro-Enkephalin or fragments thereof of at least 5 amino acids. In a specific embodiment said at least one binder binds to a region with the sequences selected from the group comprising SEQ ID No. 1, 2, 3, 4, 5, 6, 7, 8, 9 and 10. In a specific embodiment said binder do not bind to enkephalin peptides [Met]enkephalin SEQ ID No:3, and [Leu]enkephalin. SEQ ID No:4. In a specific embodiment said at least one binder binds to a region with the sequences selected from the group comprising SEQ ID No. 1, 2, 5, 6, 7, 8, 9 and 10. In another specific embodiment said at least one binder binds to a region with the sequences selected from the group comprising SEQ ID No. 2, 5, 6, and 10. In another very specific embodiment said binder bind to Pro-Enkephalin 119-159, Mid regional Pro-Enkephalin-fragment, MRPENK.

In a more specific embodiment the at least one binder binds to a region within the amino acid sequence of Pro-Enkephalin 119-159, Mid regional Pro-Enkephalin-fragment, MRPENK (SEQ ID No. 6) in a bodily fluid obtained from said subject, more specifically to to aminoacid 133-140 (LKELLETG, SEQ ID No. 13) and/or aminoacid 152-159 (SDNEEEVS, SEQ ID NO. 14) wherein each of said regions comprises at least 4 or 5 amino acids.

Thus, according to the present methods the level of immunoreactivity of the above binder is determined in a bodily fluid obtained from said subject. Level of immunoreactivity means the concentration of an analyte determined quantitatively, semi-quantitatively or qualitatively by a binding reaction of a binder to such analyte, where preferably the binder has an affinity constant for binding to the analyte of at least $10^8$ $M^{-1}$, and the binder may be an antibody or an antibody fragment or an non.IgG scaffold, and the binding reaction is an immunoassay.

The present methods using PENK and fragments thereof, especially MRPENK, are far superior over the methods and biomarkers used according to the prior art for (a) diagnosing or monitoring kidney function in subject or (b) diagnosing kidney dysfunction in a subject or (c) predicting or monitoring the risk of an adverse events in a diseased subject wherein said adverse event is selected from the group comprising worsening of kidney dysfunction including kidney failure, loss of kidney function and end-stage kidney disease or death due to kidney dysfunction including kidney failure, loss of kidney function and end-stage kidney disease or (d) predicting or monitoring the success of a therapy or intervention. First of all PENK and fragments thereof as biomarker for the before mentioned uses is an inflammation independent marker. That is an important feature as most of the known kidney biomarker like NGAL and KIM are inflammation dependent, meaning if the subject has an inflammation, e.g. in sepsis, the elevation of NGAL or KIM may be either due to inflammation or to kidney function/dysfunction. Thus, no differential diagnosis may be conducted, at least not by using a simple cut-off value (meaning one (1) cut-off value), which is independent from the particular patient population investigated. For NGAL and KIM each and every patient has an "individual" threshold for kidney function/dysfunction depending on the inflammation status of said subject which makes clinical application of these kidney markers difficult in some diseases and impossible in others. In contrast thereto one single threshold that is independent of the inflammation status of the subject may be used according to the present methods for all subjects. This makes the present methods suitable for clinical routine in contrast to the before-mentioned marker.

PENK and fragments thereof as biomarker in the methods of the present invention, especially MRPENK reflects "real" kidney function in contrast to NGAL and KIM, they reflect kidney damage and inflammation.

Thus, subject matter of the present invention is method for (a) diagnosing or monitoring kidney function in subject or (b) diagnosing kidney dysfunction in a subject or (c) predicting or monitoring the risk of an adverse events in a diseased subject wherein said adverse event is selected from the group comprising worsening of kidney dysfunction including kidney failure, loss of kidney function and end-stage kidney disease or death due to kidney dysfunction including kidney failure, loss of kidney function and end-stage kidney disease or (d) predicting or monitoring the success of a therapy or intervention with the before mentioned steps and features wherein an inflammation status independent threshold is used.

Another advantage of the above methods and the use of PENK and fragments as biomarker in the methods for (a) diagnosing or monitoring kidney function in subject or (b) diagnosing kidney dysfunction in a subject or (c) predicting or monitoring the risk of an adverse events in a diseased subject wherein said adverse event is selected from the group comprising worsening of kidney dysfunction including kidney failure, loss of kidney function and end-stage kidney disease or death due to kidney dysfunction including kidney failure, loss of kidney function and end-stage kidney disease or (d) predicting or monitoring the success of a therapy or intervention is that PENK and fragments as biomarker are very early biomarker for kidney function, kidney dysfunction, risk of an adverse event, success of a therapy or intervention. Very early means e.g. earlier than creatinin, earlier than NGAL.

One clear indication of the superiority of PENK over creatinine comes from an analysis of the association of the respective concentrations determined in critically ill patients on the day of admission with their 7 day mortality rate: PENK concentrations of survivors differ significantly from non-survivors, whereas this is not the case for creatinine clearance. Mortality in such patient population is mainly driven by loss of kidney function. Thus, the significant and much stronger association of PENK with mortality than of creatinine clearance supports the superiority of PENK over creatinine clearance as kidney dysfunction marker.

Subject of the present invention is also a method for (a) diagnosing or monitoring kidney function in subject or (b) diagnosing kidney dysfunction in a subject or (c) predicting or monitoring the risk of an adverse events in a diseased subject wherein said adverse event is selected from the group comprising worsening of kidney dysfunction including kidney failure, loss of kidney function and end-stage kidney disease or death due to kidney dysfunction including kidney failure, loss of kidney function and end-stage kidney disease or (d) predicting or monitoring the success of a therapy or intervention supporting or replacing kidney function comprising various methods of renal replacement therapy including but not limited to hemodialysis, peritoneal dialysis, hemofiltration and renal transplantation according to any of the preceding embodiments, wherein the level of pro-Enkephalin or fragments thereof of at least 5 amino acids in a bodily fluid obtained from said subject either alone or in conjunction with other prognostically useful laboratory or clinical parameters is used which may be selected from the following alternatives:

- Comparison with the median of the level of Pro-Enkephalin or fragments thereof of at least 5 amino acids in a bodily fluid obtained from said subject in an ensemble of pre-determined samples in a population of "healthy" or "apparently healthy" subjects,
- Comparison with a quantile of the level of Pro-Enkephalin or fragments thereof of at least 5 amino acids in a bodily fluid obtained from said subject in an ensemble of pre-determined samples in a population of "healthy" or "apparently healthy" subjects,
- Calculation based on Cox Proportional Hazards analysis or by using Risk index calculations such as the NRI (Net Reclassification Index) or the IDI (Integrated Discrimination Index).

Said additionally at least one clinical parameter may be determined selected from the group comprising: age, NGAL, Cystatin C, Creatinine Clearance, Creatinin, Urea and Apache Score.

In one embodiment of the invention said method is performed more than once in order to monitor the function or dysfunction or risk of said subject or in order to monitor the course of treatment of kidney and/or disease. In one specific embodiment said monitoring is performed in order to evaluate the response of said subject to preventive and/or therapeutic measures taken.

In one embodiment of the invention the method is used in order to stratify said subjects into risk groups.

Subject matter of the invention is further an assay for determining Pro-Enkephalin and Pro-Enkephalin fragments in a sample comprising two binders that bind to two different regions within the region of Pro-Enkephalin that is aminoacid 133-140 (LKELLETG, SEQ ID NO. 13) and aminoacid 152-159 (SDNEEEVS, SEQ ID NO. 14) wherein each of said regions comprises at least 4 or 5 amino acids.

In one embodiment of the assays for determining Pro-Enkephalin or Pro-Enkephalin fragments in a sample according to the present invention the assay sensitivity of said assay is able to quantify the Pro-Enkephalin or Pro-Enkephalin fragments of healthy subjects and is <15 pmol/, preferably <10 pmol/L and more preferably L<6 pmol/L.

In one embodiment of the assays for determining Pro-Enkephalin or Pro-Enkephalin fragments in a sample according to the present invention said binder exhibits an binding affinity to Pro-Enkephalin of at least $10^7$ $M^{-1}$, preferred $10^8$ $M^{-1}$, preferred affinity constant is lower than $10^9$ $M^{-1}$, most preferred lower than $10^{10}$ $M^{-1}$. A person skilled $_{[K1]}$ in the art knows that it may be considered to compensate lower affinity by applying a higher dose of compounds and this measure would not lead out-of-the-scope of the invention binding affinity may be determined as described above.

In one embodiment of the invention it may be a so-called POC-test (point-of-care), that is a test technology which allows performing the test within less than 1 hour near the patient without the requirement of a fully automated assay system. One example for this technology is the immunochromatographic test technology.

In one embodiment of the invention such an assay is a sandwich immunoassay using any kind of detection technology including but not restricted to enzyme label, chemiluminescence label, electrochemiluminescence label, preferably a fully automated assay. In one embodiment of the invention such an assay is an enzyme labeled sandwich assay. Examples of automated or fully automated assay comprise assays that may be used for one of the following systems: Roche Elecsys®, Abbott Architect®, Siemens Centauer®, Brahms Kryptor®, Biomerieux Vidas®, Alere Triage®.

A variety of immunoassays are known and may be used for the assays and methods of the present invention, these include: radioimmunoassays ("RIA"), homogeneous enzyme-multiplied immunoassays ("EMIT"), enzyme linked immunoadsorbent assays ("ELISA"), apoenzyme reactivation immunoassay ("ARIS"), dipstick immunoassays and immuno-chromotography assays.

In one embodiment of the invention at least one of said two binders is labeled in order to be detected.

The preferred detection methods comprise immunoassays in various formats such as for instance radioimmunoassay (RIA), chemiluminescence- and fluorescence-immunoassays, Enzyme-linked immunoassays (ELISA), Luminex-based bead arrays, protein microarray assays, and rapid test formats such as for instance immunochromatographic strip tests.

In a preferred embodiment said label is selected from the group comprising chemiluminescent label, enzyme label, fluorescence label, radioiodine label.

The assays can be homogenous or heterogeneous assays, competitive and non-competitive assays. In one embodiment, the assay is in the form of a sandwich assay, which is a non-competitive immunoassay, wherein the molecule to be detected and/or quantified is bound to a first antibody and to a second antibody. The first antibody may be bound to a solid phase, e.g. a bead, a surface of a well or other container, a chip or a strip, and the second antibody is an antibody which is labeled, e.g. with a dye, with a radioisotope, or a reactive or catalytically active moiety. The amount of labeled antibody bound to the analyte is then measured by an appropriate method. The general composition and procedures involved with "sandwich assays" are well-established and known to the skilled person (23).

In another embodiment the assay comprises two capture molecules, preferably antibodies which are both present as dispersions in a liquid reaction mixture, wherein a first labelling component is attached to the first capture molecule, wherein said first labelling component is part of a labelling system based on fluorescence- or chemiluminescence-quenching or amplification, and a second labelling component of said marking system is attached to the second capture molecule, so that upon binding of both capture molecules to the analyte a measurable signal is generated that allows for the detection of the formed sandwich complexes in the solution comprising the sample.

In another embodiment, said labeling system comprises rare earth cryptates or rare earth chelates in combination with fluorescence dye or chemiluminescence dye, in particular a dye of the cyanine type.

In the context of the present invention, fluorescence based assays comprise the use of dyes, which may for instance be selected from the group comprising FAM (5- or 6-carboxyfluorescein), VIC, NED, Fluorescein, Fluoresceinisothiocyanate (FITC), IRD-700/800, Cyanine dyes, auch as CY3, CY5, CY3.5, CY5.5, Cy7, Xanthen, 6-Carboxy-2',4',7',4,7-hexachlorofluorescein (HEX), TET, 6-Carboxy-4',5'-dichloro-2',7'-dimethodyfluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), Rhodamine, Rhodamine Green, Rhodamine Red, Rhodamine 110, BODIPY dyes, such as BODIPY TMR, Oregon Green, Coumarines such as Umbelliferone, Benzimides, such as Hoechst 33258; Phenanthridines, such as Texas Red, Yakima Yellow, Alexa Fluor, PET, Ethidiumbromide, Acridinium dyes, Carbazol dyes, Phenoxazine dyes, Porphyrine dyes, Polymethin dyes, and the like.

In the context of the present invention, chemiluminescence based assays comprise the use of dyes, based on the physical principles described for chemiluminescent materials in (24). Preferred chemiluminescent dyes are acridiniumesters.

As mentioned herein, an "assay" or "diagnostic assay" can be of any type applied in the field of diagnostics. Such an assay may be based on the binding of an analyte to be detected to one or more capture probes with a certain affinity. Concerning the interaction between capture molecules and target molecules or molecules of interest, the affinity constant is preferably greater than $10^1 \, M^{-1}$.

In the context of the present invention, "binder molecules" are molecules which may be used to bind target molecules or molecules of interest, i.e. analytes (i.e. in the context of the present invention PENK and fragments thereof), from a sample. Binder molecules must thus be shaped adequately, both spatially and in terms of surface features, such as surface charge, hydrophobicity, hydrophilicity, presence or absence of lewis donors and/or acceptors, to specifically bind the target molecules or molecules of interest. Hereby, the binding may for instance be mediated by ionic, van-der-Waals, pi-pi, sigma-pi, hydrophobic or hydrogen bond interactions or a combination of two or more of the aforementioned interactions between the capture molecules and the target molecules or molecules of interest. In the context of the present invention, binder molecules may for instance be selected from the group comprising a nucleic acid molecule, a carbohydrate molecule, a PNA molecule, a protein, an antibody, a peptide or a glycoprotein. Preferably, the binder molecules are antibodies, including fragments thereof with sufficient affinity to a target or molecule of interest, and including recombinant antibodies or recombinant antibody fragments, as well as chemically and/or biochemically modified derivatives of said antibodies or fragments derived from the variant chain with a length of at least 12 amino acids thereof.

Chemiluminescent label may be acridinium ester label, steroid labels involving isoluminol labels and the like.

Enzyme labels may be lactate dehydrogenase (LDH), creatinekinase (CPK), alkaline phosphatase, aspartate aminotransferace (AST), alanine aminotransferace (ALT), acid phosphatase, glucose-6-phosphate dehydrogenase and so on.

In one embodiment of the invention at least one of said two binders is bound to a solid phase as magnetic particles, and polystyrene surfaces.

In one embodiment of the assays for determining Pro-Enkephalin or Pro-Enkephalin fragments in a sample according to the present invention such assay is a sandwich assay, preferably a fully automated assay. It may be an ELISA fully automated or manual. It may be a so-called POC-test (point-of-care). Examples of automated or fully automated assay comprise assays that may be used for one of the following systems: Roche Elecsys®, Abbott Architect®, Siemens Centauer®, Brahms Kryptor®, Biomerieux Vidas®, Alere Triage®. Examples of test formats are provided above.

In one embodiment of the assays for determining Pro-Enkephalin or Pro-Enkephalin fragments in a sample according to the present invention at least one of said two binders is labeled in order to be detected. Examples of labels are provided above.

In one embodiment of the assays for determining Pro-Enkephalin or Pro-Enkephalin fragments in a sample according to the present invention at least one of said two binders is bound to a solid phase. Examples of solid phases are provided above.

In one embodiment of the assays for determining Pro-Enkephalin or Pro-Enkephalin fragments in a sample according to the present invention said label is selected from the group comprising chemiluminescent label, enzyme label, fluorescence label, radioiodine label. A further subject of the present invention is a kit comprising an assay according to the present invention wherein the components of said assay may be comprised in one or more container.

In one embodiment subject matter of the present invention is a point-of-care device for performing a method according to the invention wherein said point of care device comprises at least one antibody or antibody fragment directed to either aminoacid 133-140 (LKELLETG, SEQ ID No. 13) or aminoacid 152-159 (SDNEEEVS, SEQ ID NO. 14) wherein each of said regions comprises at least 4 or 5 amino acids.

In one embodiment subject matter of the present invention is a point-of-care device for performing a method according to the invention wherein said point of care device comprises at least two antibodies or antibody fragments directed to aminoacid 133-140 (LKELLETG, SEQ ID No. 13) and aminoacid 152-159 (SDNEEEVS, SEQ ID NO. 14) wherein each of said regions comprises at least 4 or 5 amino acids.

In one embodiment subject matter of the present invention is a kit or performing a method according to the invention wherein said point of care device comprises at least one antibody or antibody fragment directed to either aminoacid 133-140 (LKELLETG, SEQ ID No. 13) or aminoacid 152-159 (SDNEEEVS, SEQ ID NO. 14) wherein each of said regions comprises at least 4 or 5 amino acids.

In one embodiment subject matter of the present invention is a kit for performing a method according to the invention wherein said point of care device comprises at least two antibodies or antibody fragments directed to aminoacid 133-140 (LKELLETG, SEQ ID No. 13) and aminoacid 152-159 (SDNEEEVS, SEQ ID NO. 14) wherein each of said regions comprises at least 4 or 5 amino acids.

EXAMPLES

Example 1

Development of Antibodies
Peptides
Peptides were synthesized (JPT Technologies, Berlin, Germany).
Peptides/Conjugates for Immunization:
Peptides for immunization were synthesized (JPT Technologies, Berlin, Germany) with an additional N-terminal Cystein residue for conjugation of the peptides to bovine serum albumin (BSA). The peptides were covalently linked to BSA by using Sulfo-SMCC (Perbio-science, Bonn, Germany). The coupling procedure was performed according to the manual of Perbio.

TABLE 1

| Peptide for immunization | Pro-Enkephalin-sequence |
|---|---|
| (C)DAEEDD | 119-125 |
| (C)EEDDSLANSSDLLK | 121-134 |
| (C)LKELLETG | 133-140 |
| (C)TGDNRERSHHQDGSDNE | 139-155 |
| (C)SDNEEEVS | 152-159 |

The antibodies were generated according to the following method:
A BALB/c mouse was immunized with 100 µg peptide-BSA-conjugate at day 0 and 14 (emulsified in 100 µl complete Freund's adjuvant) and 50 µg at day 21 and 28 (in 100 µl incomplete Freund's adjuvant). Three days before the fusion experiment was performed, the animal received 50 µg of the conjugate dissolved in 100 µl saline, given as one intraperitonal and one intravenous injection.

Spenocytes from the immunized mouse and cells of the myeloma cell line SP2/0 were fused with 1 ml 50% polyethylene glycol for 30 s at 37° C. After washing, the cells were seeded in 96-well cell culture plates. Hybrid clones were selected by growing in HAT medium [RPMI 1640 culture medium supplemented with 20% fetal calf serum and HAT-supplement]. After two weeks the HAT medium is replaced with HT Medium for three passages followed by returning to the normal cell culture medium.

The cell culture supernatants were primary screened for antigen specific IgG antibodies three weeks after fusion. The positive tested microcultures were transferred into 24-well plates for propagation. After retesting the selected cultures were cloned and recloned using the limiting-dilution technique and the isotypes were determined.

(Lane, R. D. "A short-duration polyethylene glycol fusiontechnique for increasing production of monoclonal antibody-secreting hybridomas", J. Immunol. Meth. 81: 223-228; (1985), Ziegler, B. et al. "Glutamate decarboxylase (GAD) is not detectable on the surface of rat islet cells examined by cytofluorometry and complement-dependent antibody-mediated cytotoxicity of monoclonal GAD antibodies", Horm. Metab. Res. 28: 11-15, (1996)).

Monoclonal Antibody Production
Antibodies were produced via standard antibody production methods (Marx et al., Monoclonal Antibody Production (1997), ATLA 25, 121) and purified via Protein A-chromatography. The antibody purities were >95% based on SDS gel electrophoresis analysis.

Labelling and Coating of Antibodies.
All antibodies were labelled with acridinium ester according the following procedure: Labelled compound (tracer): 100 µg (100 µl) antibody (1 mg/ml in PBS, pH 7.4), was mixed with 10 µl Acridinium NHS-ester (1 mg/ml in acetonitrile, InVent GmbH, Germany) (EP 0353971) and incubated for 20 min at room temperature. Labelled antibody was purified by gel-filtration HPLC on Bio-Sil SEC 400-5 (Bio-Rad Laboratories, Inc., USA) The purified labelled antibody was diluted in (300 mmol/l potassiumphosphate, 100 mmol/l NaCl, 10 mmol/l Na-EDTA, 5 g/l bovine serum albumin, pH 7.0). The final concentration was approx. 800.000 relative light units (RLU) of labelled compound (approx. 20 ng labeled antibody) per 200 µl. Acridiniumester chemiluminescence was measured by using an AutoLumat LB 953 (Berthold Technologies GmbH & Co. KG).

Solid Phase Antibody (Coated Antibody):
Solid phase: Polystyrene tubes (Greiner Bio-One International AG, Austria) were coated (18 h at room temperature) with antibody (1.5 µg antibody/0.3 ml 100 mmol/l NaCl, 50 mmol/l Tris/HCl, pH 7.8). After blocking with 5% bovine serum albumine, the tubes were washed with PBS, pH 7.4 and vacuum dried.

Antibody Specificity

TABLE 2

| Peptide for immunization | Pre-Pro-Enkephalin-sequence | Antibody name |
|---|---|---|
| (C)DAEEDD | 119-125 | NT-MRPENK |
| (C)EEDDSLANSSDLLK | 121-134 | NM-MRPENK |
| (C)LKELLETG | 133-140 | MR-MRPENK |
| (C)TGDNRERSHHQDGSDNE | 139-155 | MC-MRPENK |
| (C)SDNEEEVS | 152-159 | CT-MRPENK |

Antibody Cross-Reactivities were Determined as Follows:
1ug peptide in 300 µl PBS, pH 7.4 was pipetted into Polystyrene tubes and incubated for 1h at room temperature. After incubation the tubes were washed 5 times (each 1 ml) using 5% BSA in PBS, pH 7.4. Each of the labelled antibodies were added (300 µl in PBS, pH 7.4, 800.000 RLU/300 µl) an incubated for 2 h at room temperature, After washing 5 times (each 1 ml of washing solution (20 mmol/l PBS, pH 7.4, 0.1% Triton X 100), the remaining luminescence (labelled antibody) was quantified using the AutoLumat Luminumeter 953. MRPENK-peptide was used as reference substance (100%).

The cross reactivities of the different antibodies are listed in table 3.

TABLE 3

| Antibody | DAEE DD | EEDDSLA NSSDLLK | LKEL LETG | TGDNRERS HHQDGSDNE | SDNE EEVS | MRPENK (SEQ ID NO. 6) |
|---|---|---|---|---|---|---|
| NT-MRPENK | 121 | 10 | <1 | <1 | <1 | 100 |
| NM-MRPENK | <1 | 98 | <1 | <1 | <1 | 100 |
| MR-MRPENK | <1 | <1 | 105 | <1 | <1 | 100 |
| MC-MRPENK | <1 | <1 | <1 | 115 | <1 | 100 |
| CT-MRPENK | <1 | <1 | <1 | <1 | 95 | 100 |

All antibodies bound the MRPENK peptide, comparable to the peptides which were used for immunization. Except for NT-MRPENK-antibody (10% cross reaction with EEDDSLANSSDLLK), no antibody showed a cross reaction with MR-PENK fragments not used for immunization of the individual antibody.

Pro-Enkephalin Immunoassay:

50 µl of sample (or calibrator) was pipetted into coated tubes, after adding labeled antibody (200 ul), the tubes were incubated for 2 h at 18-25° C. Unbound tracer was removed by washing 5 times (each 1 ml) with washing solution (20 mmol/l PBS, pH 7.4, 0.1% Triton X-100). Tube-bound labelled antibody was measured by using the Luminumeter 953. Using a fixed concentration of 1000 pmol/ of MRPENK. The signal (RLU at 1000 pmol MRPENK/1) to noise (RLU without MRPENK) ratio of different antibody combinations is given in table 4. All antibodies were able to generate a sandwich complex with any other antibody. Surprisingly, the strongest signal to noise ratio (best sensitivity) was generated by combining the MR-MRPENK- and CT-MRPENK antibody. Subsequently, we used this antibody combination to perform the MRPENK-immunoassay for further investigations. MR-MRPENK antibody was used as coated tube antibody and CT-MRPENK antibody was used as labelled antibody.

TABLE 4

| Labelled antibody | Solid phase antibody | | | | |
|---|---|---|---|---|---|
| | NT-MRPENK | NM-MRPENK | MR-MRPENK | MC-MRPENK | CT-MRPENK |
| NT-MRPENK | / | 27 | 212 | 232 | <1 |
| NM-MRPENK | 36 | / | 451 | 487 | <1 |
| MR-MRPENK | 175 | 306 | / | 536 | 1050 |
| MC-MRPENK | 329 | 577 | 542 | / | <1 |
| CT-MRPENK | <1 | 615 | 1117 | 516 | / |

Calibration:

The assay was calibrated, using dilutions of synthetic MRPENK, diluted in 20 mM K2PO4, 6 mM EDTA, 0.5% BSA, 50 M Amastatin, 100 NM Leupeptin, pH 8.0. Pro-Enkephalin control plasma is available at ICI-diagnostics, Berlin, Germany.

FIG. 1 shows a typical Pro-Enkephalin dose/signal curve.

The assay sensitivity was 20 determinations of 0-calibrator (no addition of MRPENK)+2SD) 5.5 pmol/L.

Creatinine Clearance

Creatinine clearance was determined using the MDRD formula (see Levey et al, 2009).

Example 2

PENK in Healthy Subjects

Healthy subjects (n=4211, average age 56 years) were measured using the MRPENK assay. The mean value was 44.7 pmol MRPENK/L, the lowest value was 9 pmol/L and the $99^{th}$ percentile was 80 pmol/L. Since the assay sensitivity was 5.5 pmol/L, 100% of all healthy subjects were detectable using the described MRPENK assay (see FIG. 2).

Pro-Enkephalin correlates with Creatinine Clearance in healthy subjects with normal kidney function.

Figure 3:
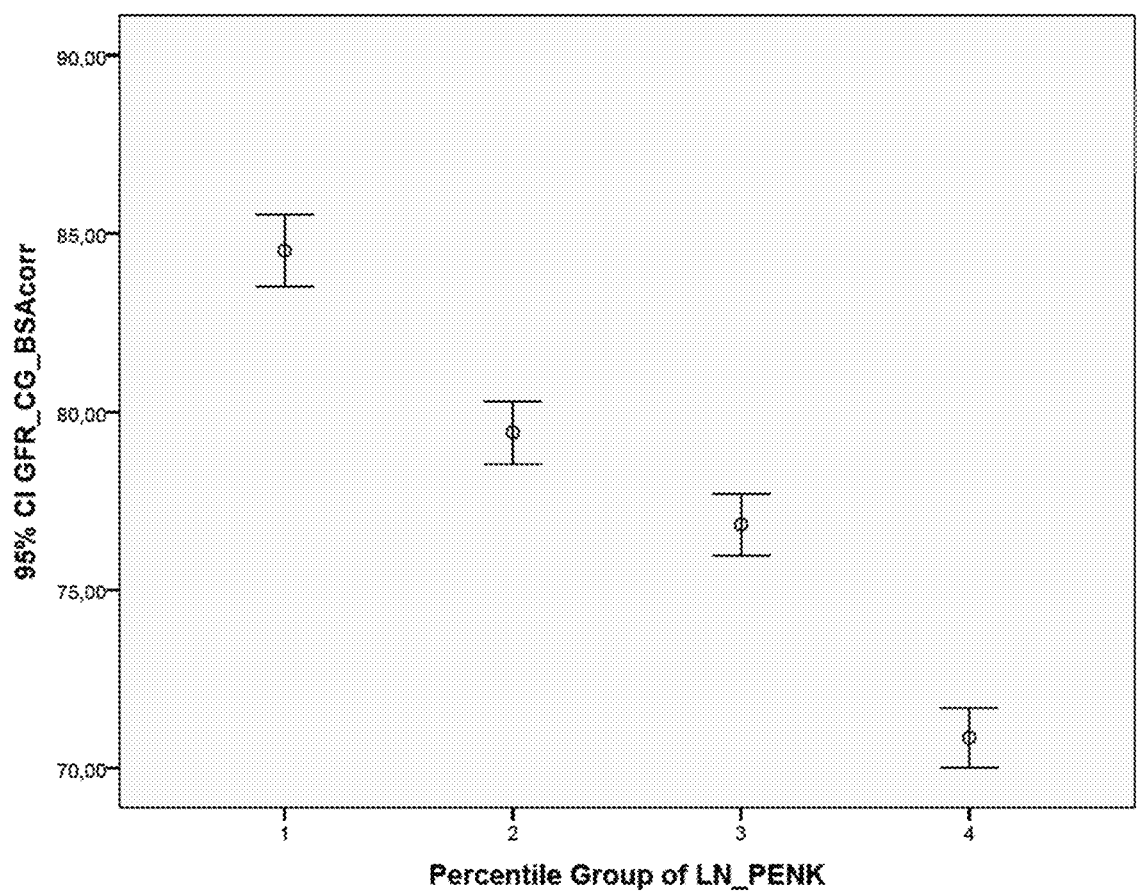

Surprisingly, Pro-Enkephalin was negatively correlated with Creatinine Clearance in healthy subjects (r=−0.33, p<0,0001), see FIG. 3. The coefficient of correlation was slightly stronger in male than in females (r=−0.34 vs −0.29, both p<0,0001). These data indicating a strong association between PENK and kidney function.

FIG. 3: correlation of creatinine clearance vs. PENK in healthy subjects. Y axis: quartiles of Creatinine Clearance, x axis: quartiles of PENK.

Example 3

Correlation of PENK and Kidney Function (Creatinine Clearance) in Patients with Chronic and Acute Diseases.

TABLE 5

| Disease | r-value | p-value |
|---|---|---|
| Chronic Heart Failure N = 122 | −0.55 | <0.0001 |
| Acute Heart Failure N = 149 | −0.68 | <0.0001 |
| Acute Myocardial Infarction N = 78 | −0.82 | <0.0001 |
| Sepsis N = 101 | −0.74 | <0.0001 |
| SIRS N = 109 | −0.79 | <0.0001 |

PENK Correlated Always Significantly with Creatinine Clearance, in Acute Diseases the Correlation was Stronger than in Chronic Diseases or in Healthy Subjects.

Example 4: PENK in Critical Ill Patients

To investigate the diagnostic performance of PENK for diagnosis of kidney failure in acute clinical settings, we performed the following clinical study:

Clinical Study

101 ED patients fulfilling the definition of sepsis (Crit Care Med. 2008 January; 36(1):296-327.) were subsequently hospitalized (average 5 days of hospitalization) and received a standard of care treatment. EDTA-plasma was generated from day 1 (ED presentation) and one sample each day during hospital stay. The time to freeze samples for later analyte-measurement was less than 4h.

Patient Characteristics are Summarized in Table 6:

TABLE 6

| Variable | all (n = 101) | in hospital deaths (n = 27) | discharged (n = 74) | p-value |
|---|---|---|---|---|
| Demographics | | | | |
| Gender - male | 60 (60) | 13 (48) | 47 (64) | 0.163 |
| Age - median [IQR] | 78 [72-72] | 77 [71.25-83] | 80 [75-84.5] | 0.142 |
| Examination variables | | | | |
| BP systolic (mmHg) - median [IQR] | 115 [100-100] | 120 [106.25-138.75] | 105 [80-120] | 0.001 |
| BP diastolic (mmHg) - median [IQR] | 65 [60-60] | 65 [60-85] | 60 [50-70] | 0.002 |
| HR - median [IQR] | 100 [94-94] | 100 [94-114.75] | 100 [93.5-107.5] | 0.407 |
| RR - median [IQR] | 24 [22-22] | 24 [22-28] | 26 [24-28] | 0.069 |
| MAP (mmHg) - median [IQR] | 83.3 [74-74] | 83.3 [77.62-100.75] | 81.6 [63.5-89] | 0.026 |
| concomitant diseases | | | | |
| Cardiovascular - yes | 26 (25.7) | 9 (33.3) | 17 (23) | 0.311 |
| Hypertensive - yes | 47 (46.5) | 13 (48.1) | 34 (45.9) | 1.000 |
| Diabetes - yes | 35 (34.7) | 9 (33.3) | 26 (35.1) | 1.000 |
| Cancere - yes | 13 (12.9) | 3 (11.1) | 10 (13.5) | 1.000 |
| routine laboratory variables | | | | |
| Blood culture - yes | 31 (31) | 5 (19) | 26 (35) | 0.246 |
| negative | 15 (16.3) | 2 (8) | 13 (19.4) | |
| positive | 16 (17.4) | 3 (12) | 13 (19.4) | |
| Creatinine clearance (ml/min) - median [IQR] | 48 [23.25-23.25] | 56 [29.25-80] | 31.5 [14.75-66] | 0.043 |
| Creatinine - median [IQR] | 1.3 [0.9-0.9] | 1.25 [0.9-2.08] | 1.8 [1-3.15] | 0.080 |
| UREA - median [IQR] | 36 [21-21] | 31.5 [20-53.25] | 51 [42-87] | 0.004 |
| GCS - median [IQR] | 15 [10-10] | 15 [12.5-15] | 8 [8-11] | <0.001 |
| Pcr - median [IQR] | 16 [6.6-6.6] | 14.5 [6.7-23.7] | 17.35 [6.6-28.05] | 0.846 |
| Gluco - median [IQR] | 113.5 [94.5-94.5] | 110 [95.5-144] | 128 [94-160.5] | 0.400 |
| biliru - median [IQR] | 0.9 [0.71-0.71] | 0.9 [0.7-1.03] | 0.91 [0.77-1.18] | 0.534 |
| GR - median [IQR] | 3.8 [3.3-3.3] | 3.8 [3.2-4.3] | 3.7 [3.4-4.2] | 0.684 |
| GB - median [IQR] | 12700 [6774-6774] | 13100 [8115-17565] | 11920 [25.55-18790] | 0.343 |
| PLT - median [IQR] | 213 [150-150] | 217 [154.75-301] | 185 [130-236.5] | 0.113 |
| HCT - median [IQR] | 32 [28-28] | 31.5 [28-37] | 34 [31.25-39.5] | 0.149 |
| Leuco/Neutr (%) - median [IQR] | 87 [80-80] | 86 [78.25-89.95] | 91 [87-93.05] | 0.001 |
| HB - median [IQR] | 10.4 [9.47-9.47] | 10.15 [9.3-12.4] | 10.85 [9.9-12.67] | 0.220 |
| Na - median [IQR] | 137 [134-134] | 137 [133-141] | 139 [134-144.5] | 0.204 |
| K - median [IQR] | 3.9 [3.5-3.5] | 3.9 [3.6-4.3] | 3.9 [3.3-5.1] | 0.982 |
| INR - median [IQR] | 1.19 [1.1-1.1] | 1.19 [1.1-1.4] | 1.18 [1.04-1.36] | 0.731 |
| TC - median [IQR] | 38.4 [36-36] | 38.5 [38.12-38.7] | 36 [35.55-38.5] | <0.001 |
| SAO2 - median [IQR] | 94 [90-90] | 95 [90.25-97] | 93 [88.5-95.5] | 0.119 |
| pH - median [IQR] | 7.45 [7.38-7.38] | 7.46 [7.4-7.5] | 7.4 [7.24-7.4] | <0.001 |
| PO2 - median [IQR] | 67 [56-56] | 66.5 [56-78] | 67 [56.5-79.5] | 0.806 |
| PCO2 - median [IQR] | 36 [32-32] | 37.5 [33-43.75] | 34 [30-41] | 0.245 |
| Lact - median [IQR] | 1.5 [1-1] | 1.3 [0.83-1.9] | 2.5 [1.4-4.15] | <0.001 |
| Bic - median [IQR] | 23.5 [21-21] | 24.25 [21.43-28] | 21 [17.35-23.25] | 0.001 |
| FiO2 (%) - median [IQR] | 21 [21-21] | 21 [21-23.25] | 24 [21-45] | <0.001 |
| other | | | | |
| Acute organ disfunction - yes | 39 (43.3) | 16 (64) | 23 (35.4) | 0.021 |
| Apache score (%) - median [IQR] | 19 [12.5-12.5] | 14.65 [12.12-20.38] | 32 [20-39] | <0.001 |
| Days hospitalized - median [IQR] | 5 [2-2] | 6 [4-7] | 2 [1-6] | 0.003 |
| treatment at baseline | | | | |
| Diuresis (cc) - median [IQR] | 900 [600-600] | 1000 [700-1200] | 450 [200-1025] | <0.001 |
| Steroids - yes | 16 (15.8) | 4 (14.8) | 12 (16.2) | 1.000 |
| Vasopressors - yes | 18 (17.8) | 13 (48.1) | 5 (6.8) | <0.001 |
| Antibiotics - yes | 101 (100) | 27 (100) | 74 (100) | 1.000 |
| Fluid therapy - yes | 101 (100) | 27 (100) | 74 (100) | 1.000 |

26.7% of all patients died during hospital stay and are counted as treatment non responder, 73.3% of all patients survived the sepsis and are counted as treatment responder.
53% off all patients presenting with sepsis had an non-normal PENK value > 80 pmol/L (99 percentile), indicating PENK not to be a marker for the infection.

Results of Clinical Study

Figure 4:
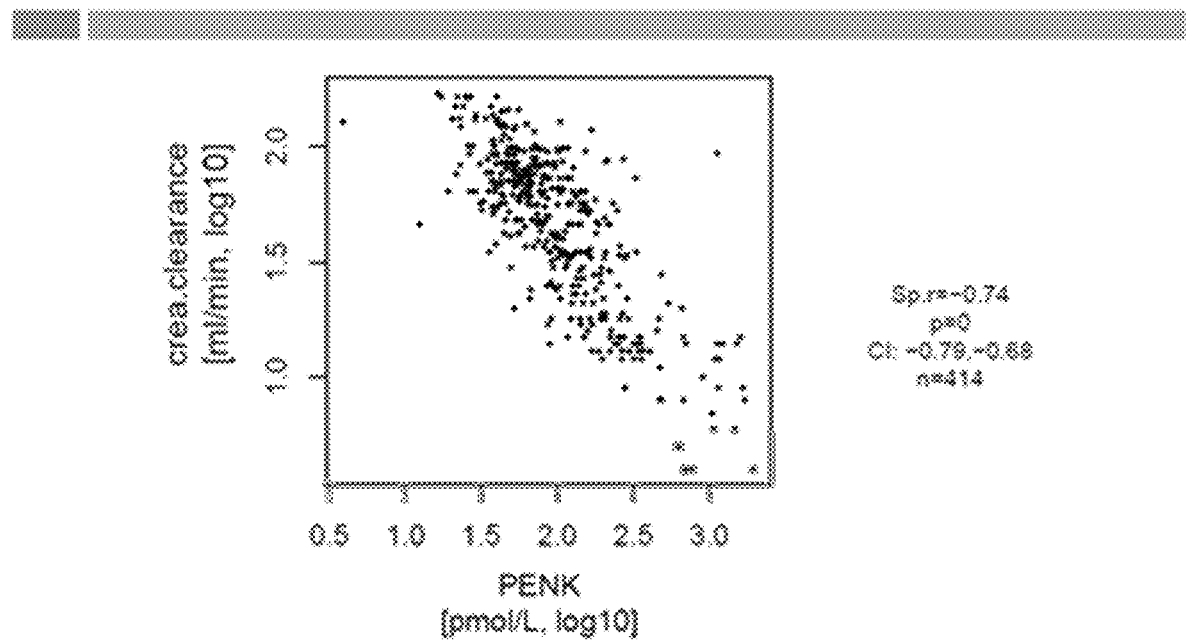

PENK highly correlated to creatinine clearance (r=−0.74, p<0,0001, FIG. 4).

Figure 5:
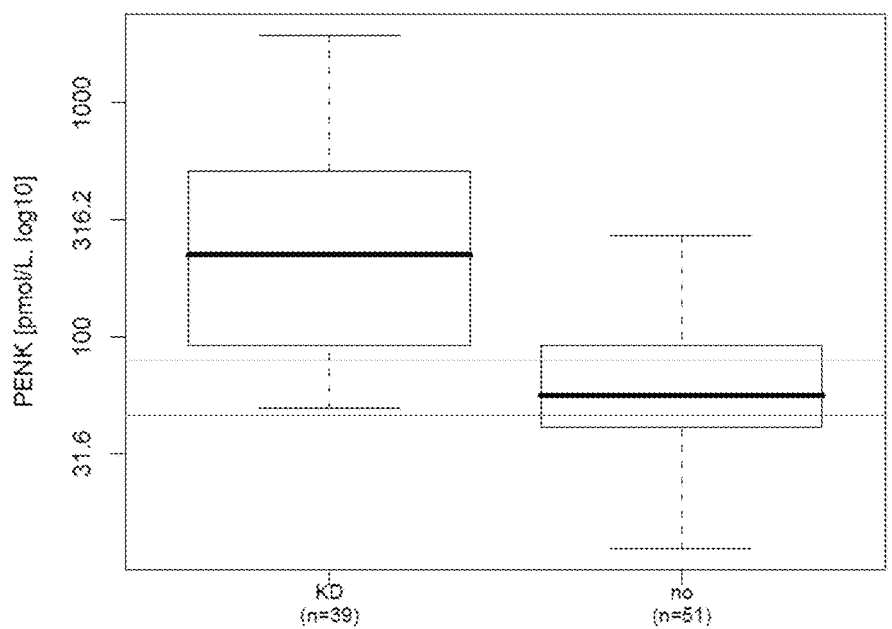
Figure 6:
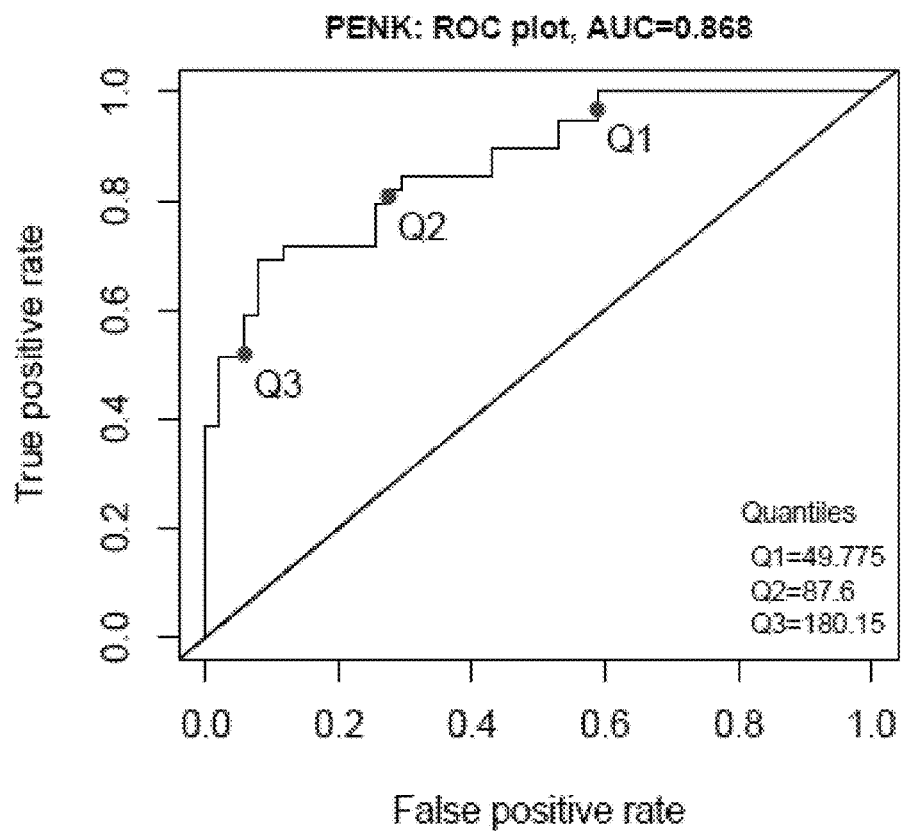

Penk Diagnoses Kidney Dysfunction:

Kidney dysfunction was defined based on the RIFLE criteria (Venkatamaran and Kellum, 2007). Patients were counted as kidney dysfunction if any of the RIFLE classification factors was fulfilled. Within the study cohort, we determined the RIFLE within 90 subjects at day 1 (presentation at ED), 39 patients fulfilled RIFLE classification (had risk of kidney disease, kidney injury, kidney failure loss of kidney function or end-stage kidney disease) and 51 patients had no kidney dysfunction. Increased PENK was significantly (p=<0.0001) correlated with kidney dysfunction (AUC: 0,868). (FIGS. 5 and 6)

To compare the diagnostic value for kidney dysfunction, we used NGAL as reference marker (Soni et al, 2010). NGAL was measured, using a commercially ELISA (NGAL Elisa kit, Bioporto, Gentofte, Denmark).

Figure 7:
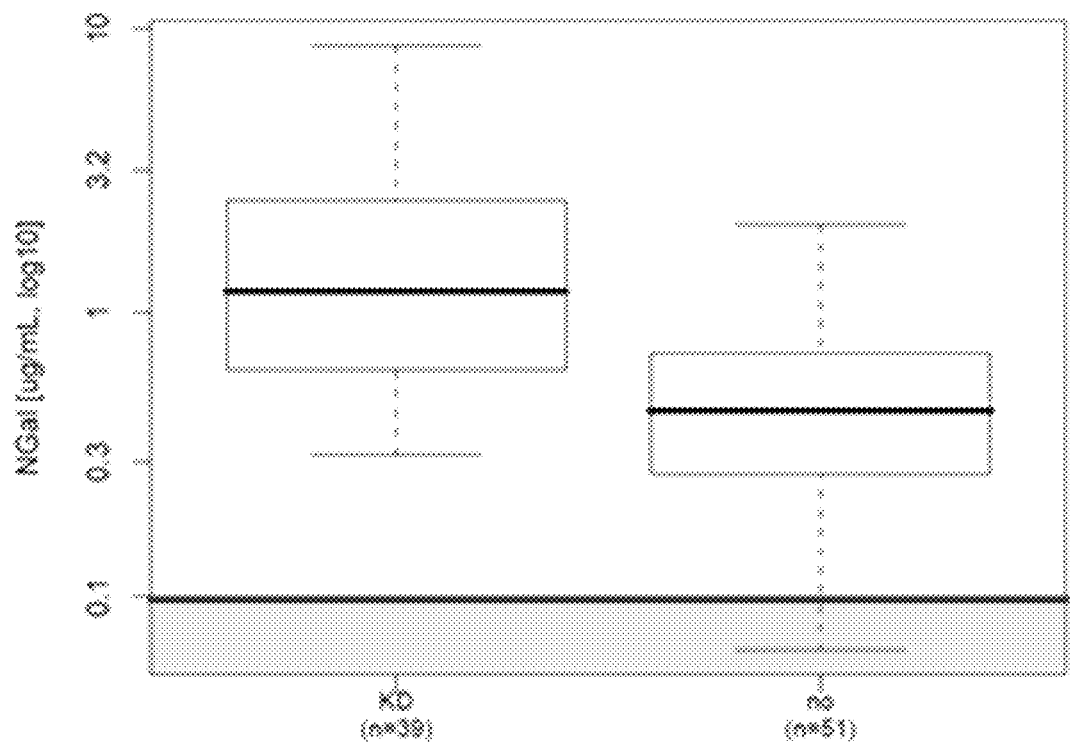
Figure 8:
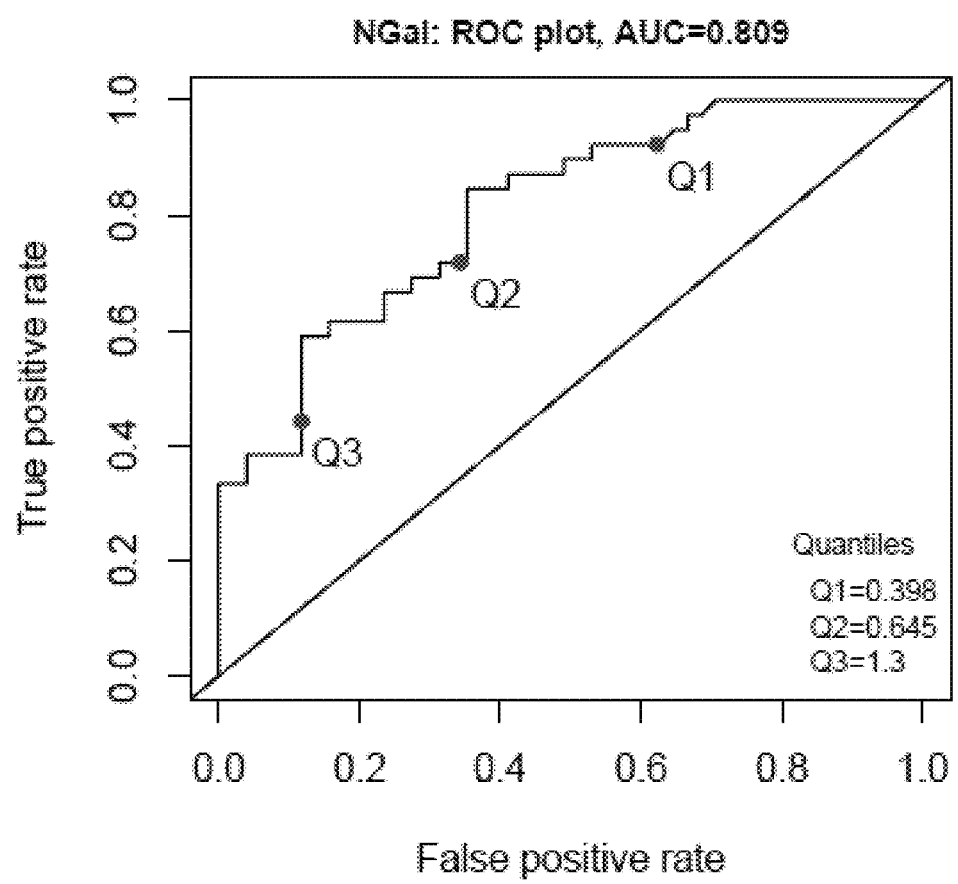

NGAL, like PENK, was significantly increased in patients with kidney dysfunction (p<0.0001), the AUC for diagnosis of kidney dysfunction was 0,809. (FIGS. 7 and 8)

Comparing PENK and NGAL showed a strong superiority of PENK vs NGAL for diagnosis of kidney dysfunction: the Chi2 value of PENK was 45.32 vs. 32.21 for NGAL, indicating a 40% improvement of diagnostic quality (specificity and sensitivity) by PENK. (Table 7) Table 7:

TABLE 7

| Model | N | Events | Model Chi2 | d.f. | LR p-value | C index [95-CI] |
|---|---|---|---|---|---|---|
| PCT | 76 | 34 | 13.02 | 1 | 0.00031 | 0.721 [0.602, 0.839] |
| Apache | 90 | 39 | 28.58 | 1 | <0.00001 | 0.778 [0.681, 0.874] |
| NGal | 90 | 39 | 32.21 | 1 | <0.00001 | 0.809 [0.723, 0.896] |
| PENK | 90 | 39 | 45.32 | 1 | <0.00001 | 0.868 [0.796, 0.94] |

Initial PENK is Highly Prognostic.

We correlated the initial PENK value with the in hospital mortality and compared PENK with APACHE 2 sepsis score (see Knaus et al, 1985, 2001) and creatinine clearance. PENK is highly prognostic for sepsis outcome (see FIG. 9) and comparable to APACHE 2 score (AUC/C index 0,744 (PENK) and 0,783 (Apache). There is a significant added information if PENK and APACHE 2 are combined (combined AUC: 0,794 FIG. 10). PENK is substantially stronger in prognosis than the creatinine clearance (AUC 0,638). Surprisingly, the prognostic value of PENK was stronger after the first day of ICU-treatment (AUC 0.79).

Cut Off-Analysis for in Hospital Death Prognosis Using Baseline Sample and 1 Sample after 1 Day of ICU Treatment.

Since the prognostic power of PENK was further improved one day after starting ICU treatment, we analyzed the PENK in serial measurements of day before ICU-treatment and 1 day after starting ICU treatment. To illustrate the clinical performance, we used a simple cut off analysis at a cut off value of 100 pmol/L.

If patients are below the cut off at hospital presentation and remain below the cut off after initiating ICU treatment, the mortality was 11% (well treated before and during hospitalization). If PENK was above the cut off at both time points, the mortality was about 5 times higher (52.5%) (not responding to treatment) and if patients present with PENK values above 100 pmol/A and reducing their PENK levels below 100 pmol/l during ICU treatment the mortality was 0 (treatment responder). These data indicate a strong association of PENK and treatment success, supporting its use for therapy follow up (serial testing).

TABLE 8

|  | mortality | N patients died vs all |
|---|---|---|
| PENK > 100 pmol/l presentation and first day after ICU treatment | 52.5% | 21/40 |
| PENK > 100 pmol/l at presentation and < 100 pmol/l first day after ICU treatment | 0% | 0/7 |
| PENK < 100 pmol/l at presentation and first day of ICU treatment | 11% | 6/54 |

Figure 11:
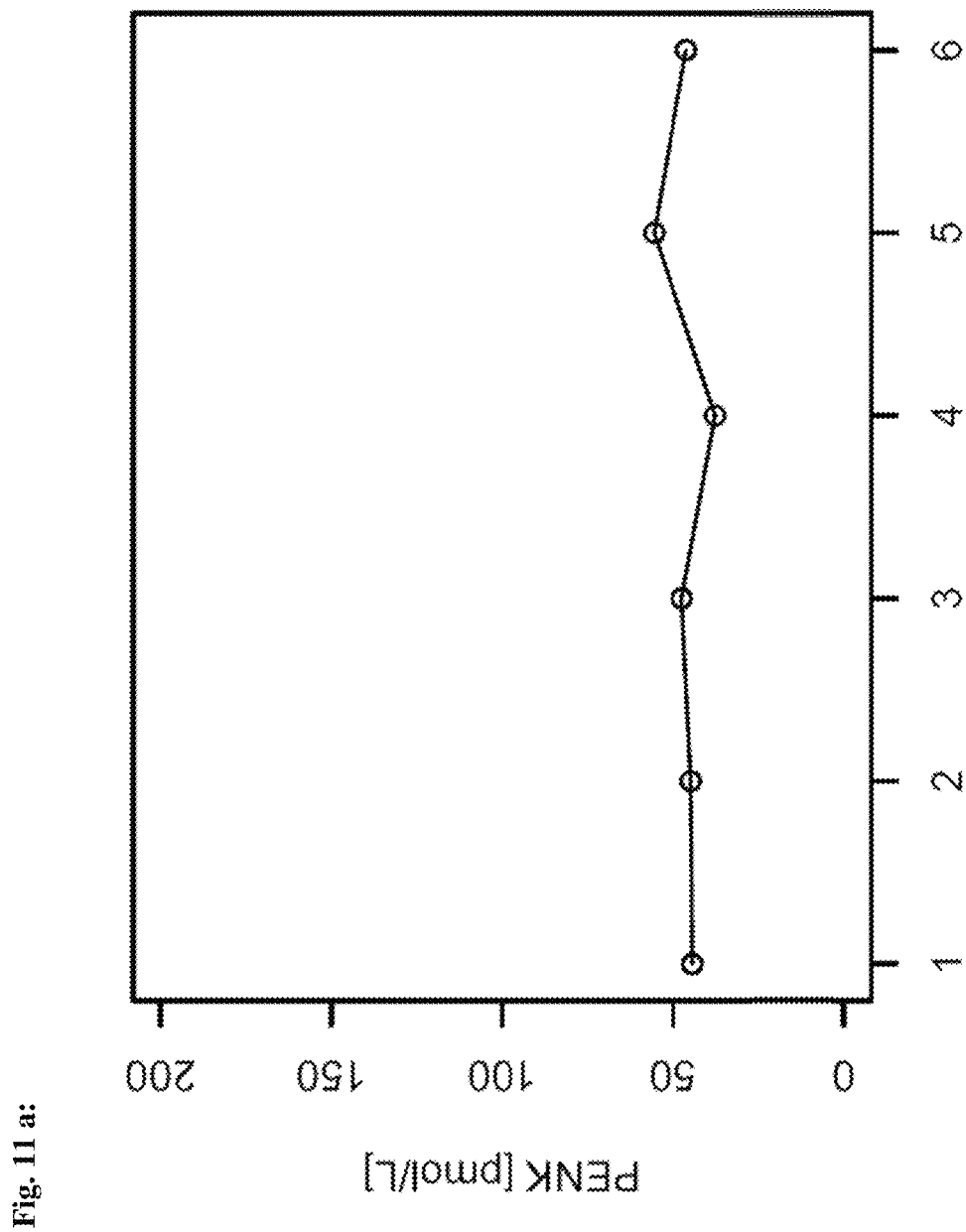
Figure 11:
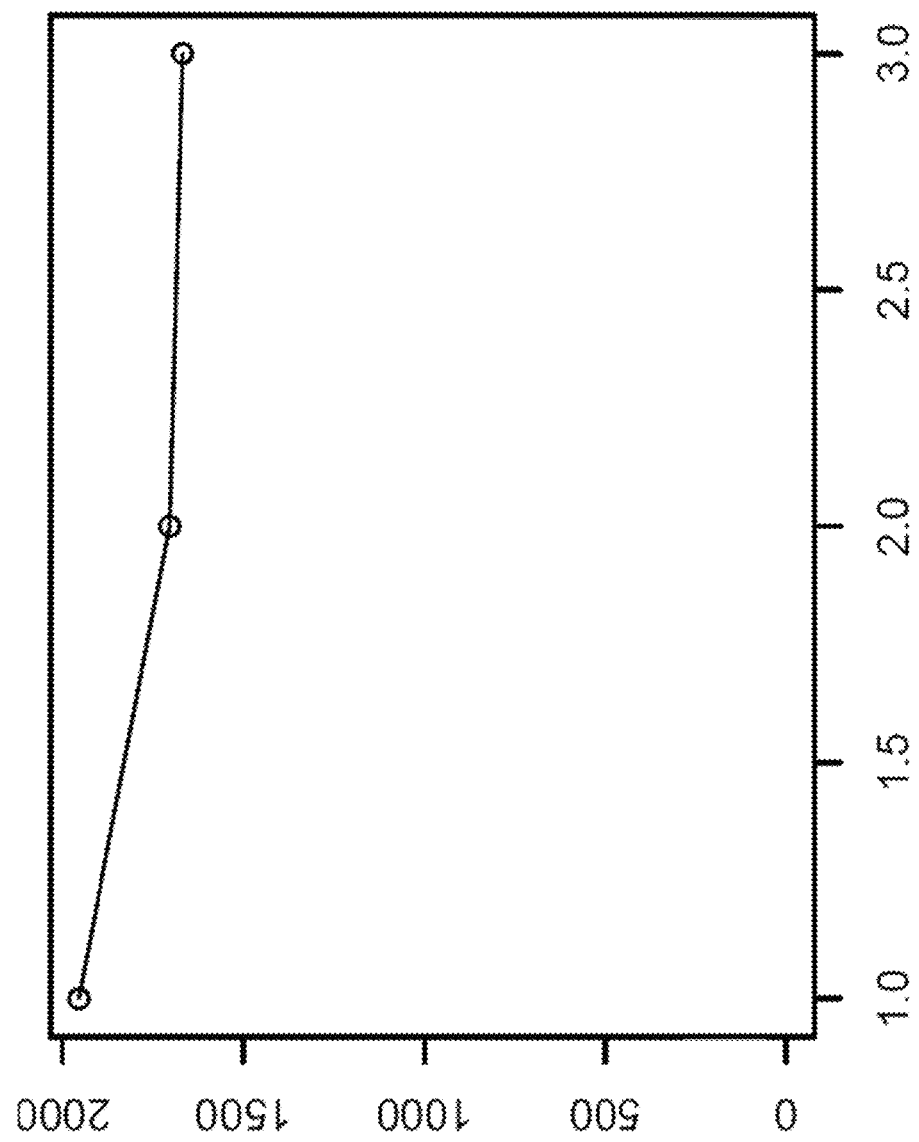
Figure 11:
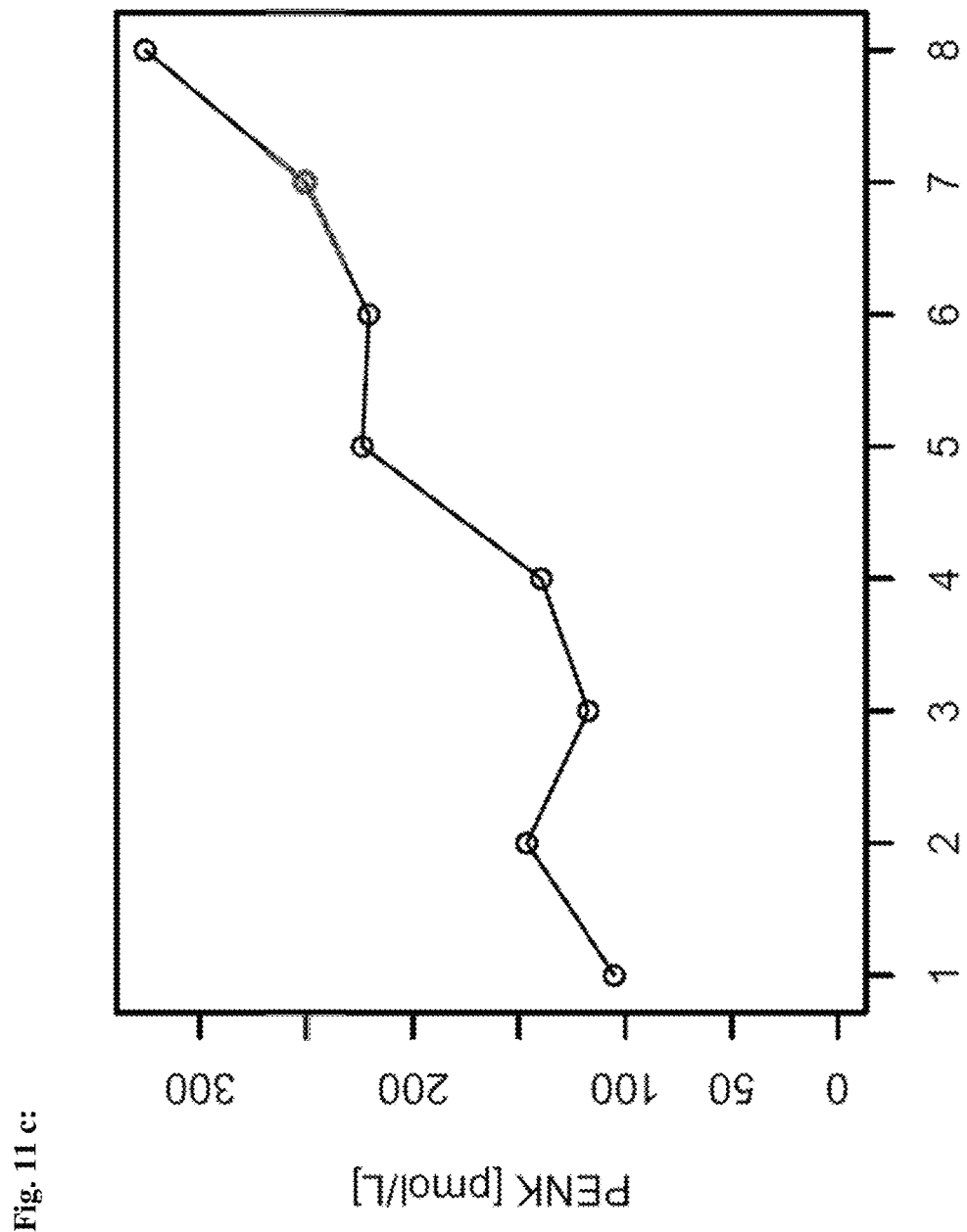
Figure 11:
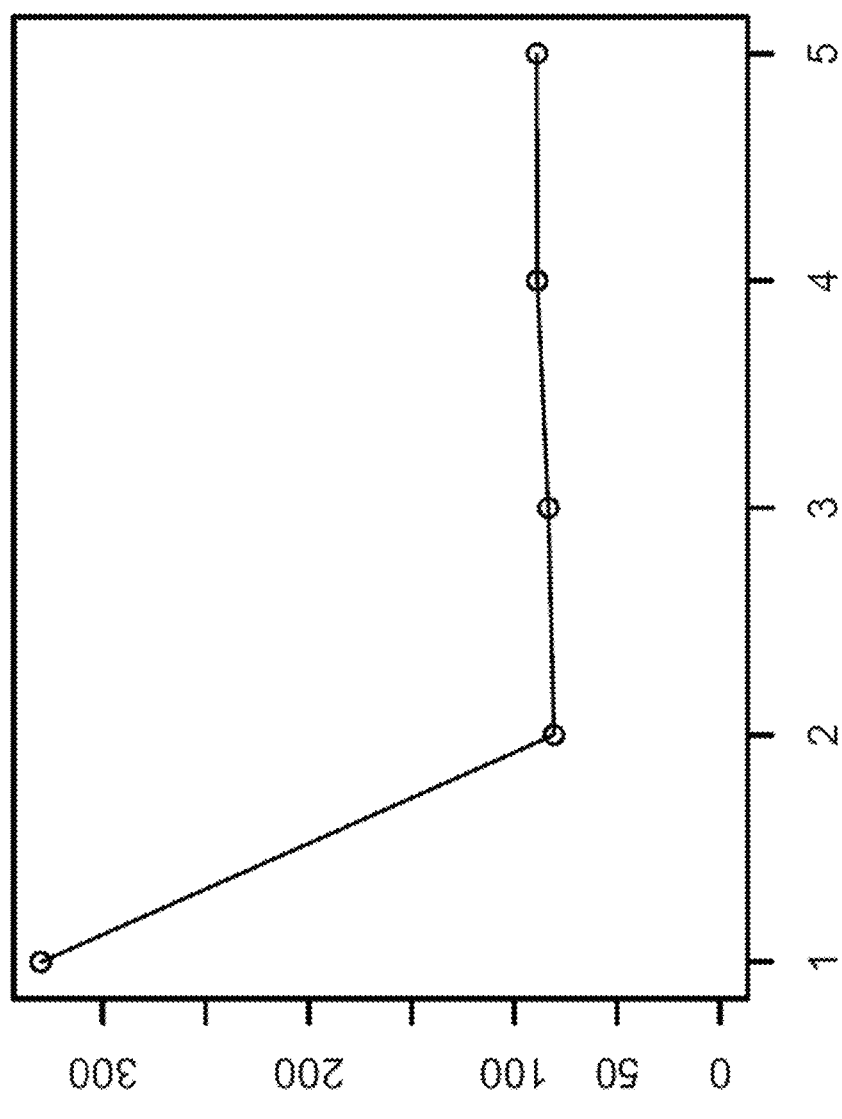

FIG. 11 a-d: examples of patient follow up measurements.
a) A patient (survivor) with initial PENK<100 pmol/L and remained <100 pmol/L during hospital stay.
b) A patient (died during hospital stay) with initial PENK>100 pmol/L and was not reduced to values <100 pmol/L.
c) A patient (died during hospital stay) with initial PENK>100 pmol/L and was not reduced to values <100 pmol/L.
d) A patient (survivor) with initial PENK>100 pmol/L, the PENK value declined to values <100 pmol/L within one day of ICU treatment.

Example 5: The Use of Serial Measurement of PENK

In the patient population described in example 4 (patients with sepsis, severe sepsis or septic shock) plasma PENK was measured on the day of admission and on the following day (day 1). Using a simple cut-off value of 100 pmol/L, which is close to the 99th percentile of the normal range, the population was segmented in two groups (above and below 100 pmol/L) and the corresponding 7 day survival rates were depicted in Kaplan-Meier-Plots (FIGS. 16 a) and b)). Patients with a PENK concentration below 100 pmol/L on the day of admission, whose PENK concentration remained below 100 pmoU/L on day 1, had a high survival rate of 87%, whereas, when their PENK concentration increased over 100 pmol/L on day 1, the survival rate was lowered to 67%. In contrast, patients with a PENK concentration above 100 pmol/L on the day of admission, whose PENK concentration remained above 100 pmol/L on day 1, had a poor survival rate of only 50%, whereas, when their PENK concentration decreased below 100 pmol/L on day 1, the survival rate was 100%.

Example 6

Figure 17:
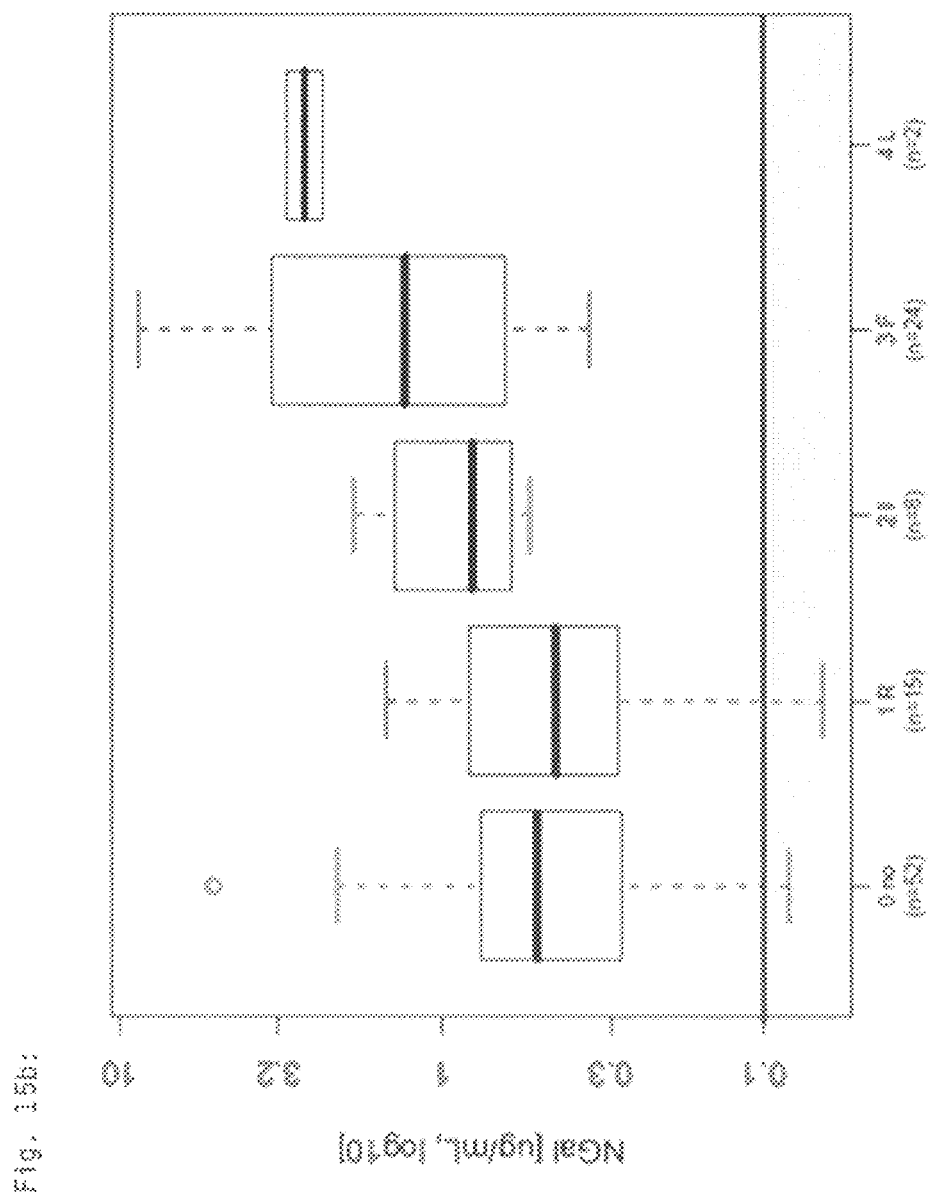

Using the plasma PENK concentrations determined in the patient population described in example 4 (patients with sepsis, severe sepsis or septic shock) on the day of admission, it was analyzed by multivariable linear regression analysis, which parameters/variables determine to which extent the PENK concentrations. In FIG. 17 the partial R2 are depicted. The analysis demonstrates that measures of kidney function (in the case shown creatinine clearance) are by far the strongest determinants for PENK concentrations.

TABLE 9

Association of variables determined in the patient population as described in example 4 on the day of admission with the 7 day mortality.

| Variable - median [IQR] | all (n = 101) | deaths within 7 days (n = 28) | 7 day survivor (n = 73) | p-value |
|---|---|---|---|---|
| PENK (pmol/L) | 87 [50-205] | 209 [77-499] | 75 [47-124] | <0.001 |
| Creatinine clearance (ng/mL) | 48 [23-77] | 33 [15-69] | 56 [29-81] | 0.071 |
| Apache score (points) | 16 [13-21] | 23 [18-27] | 14 [12-18] | <0.001 |

PENK in Males

Figure 12:
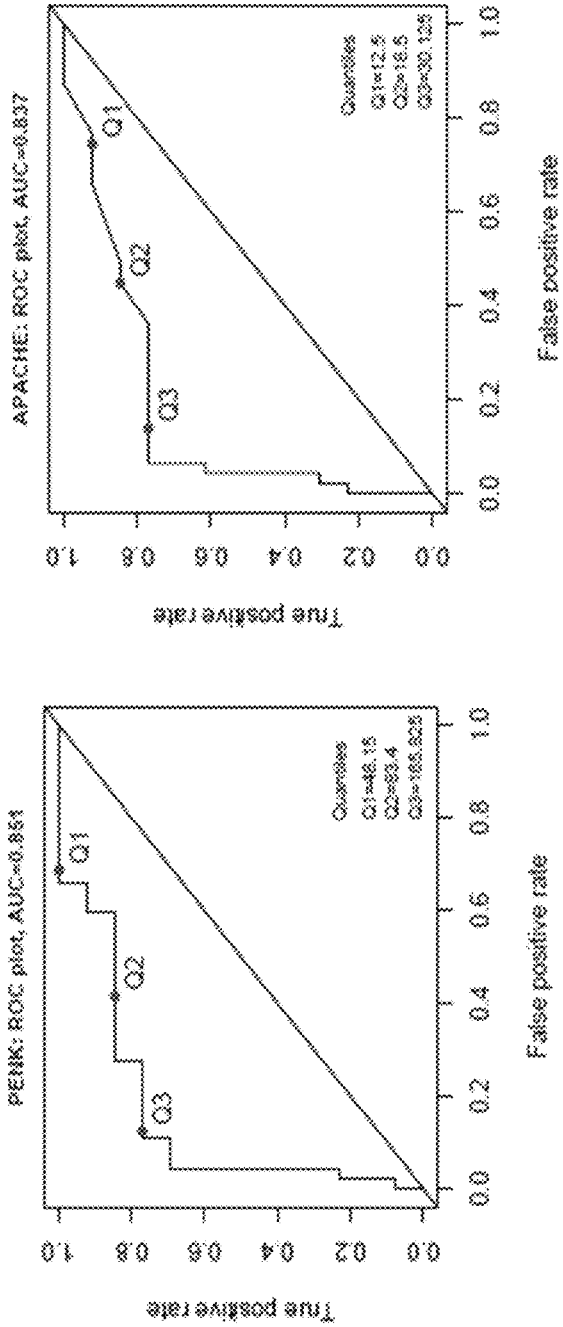
Figure 13:
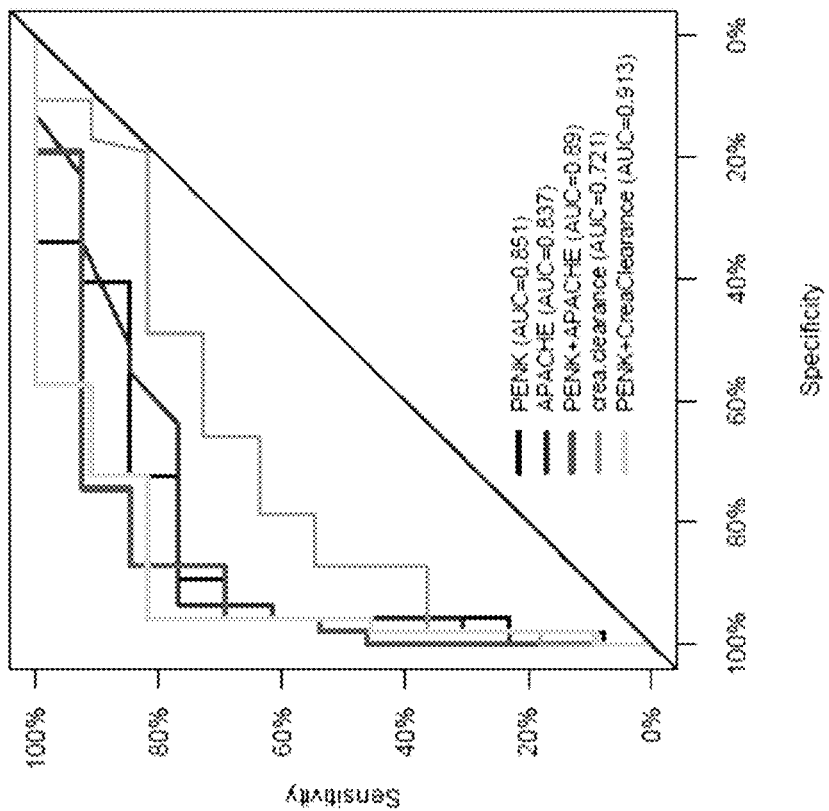
Figure 14:
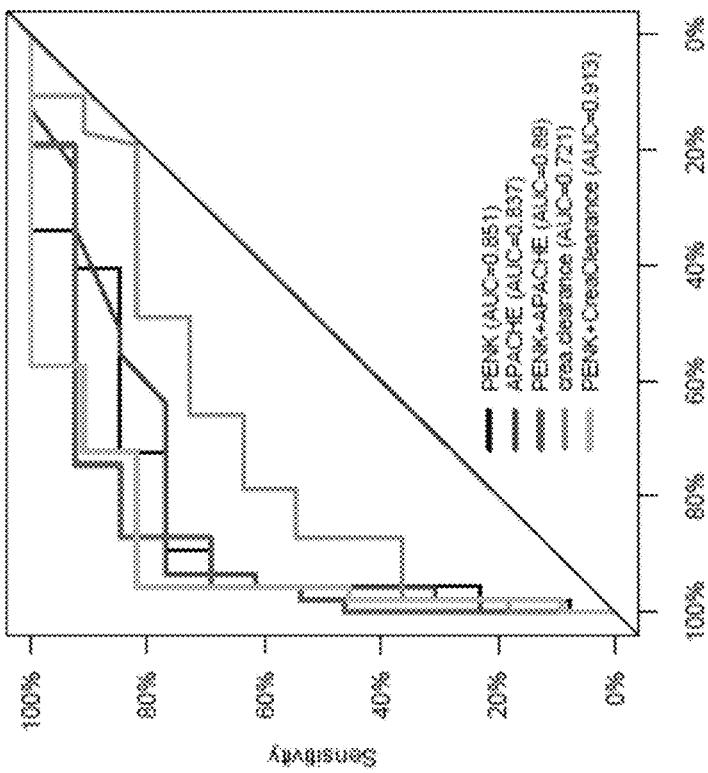

Using PENK as prognostic marker, PENK at first day (presentation at ED) was even stronger in prognosis of in hospital death in the male population (AUC 0,849, FIG. 12), a combination of PENK and Apache resulted in an AUC of 0.89 vs 0,837 Apache alone (FIG. 13). The combination of PENK and creatinine clearance generated a superior prognostic value of AUC 0.91 vs 0,721 for creatinine clearance alone (FIG. 14). As for the whole patient population, the prognostic value of PENK was stronger after the first day of ICU-treatment (day 2, AUC 0,872).

FIGURE DESCRIPTION

FIG. 1: shows a typical ProEnkephalin dose/signal curve. Standard curve proEnkephalin FIG. 2: frequence distribution of Pro Enkephalin in a healthy population (n=4211)

Figure 2:
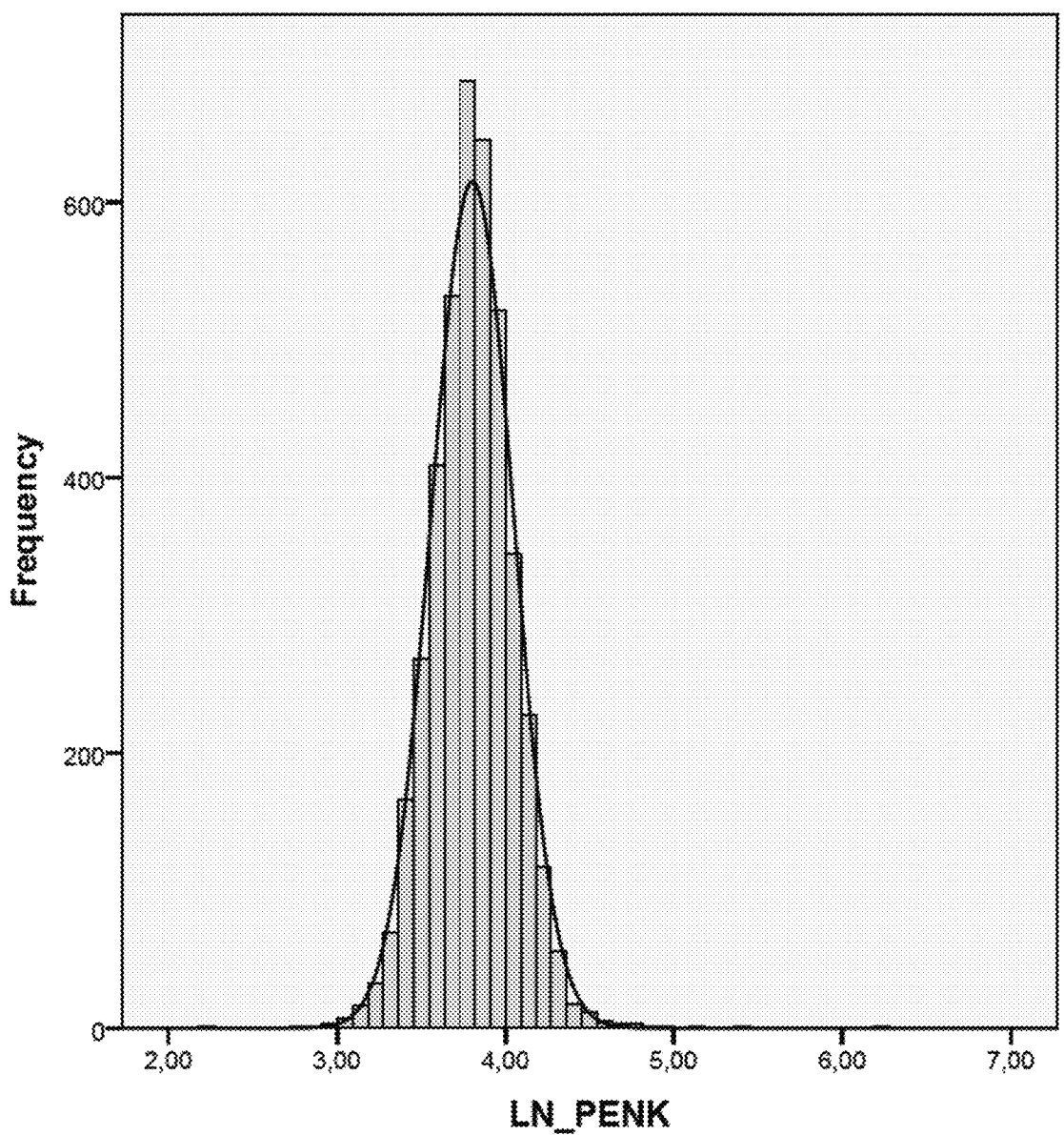

The mean value of PENK was 44.7 pmol/L, standard deviation=1.27, the 99 percentile (upper normal range) was 80 pmol PENK/L. FIG. 2 shows the LN values of PENK.

FIG. 3: Correlation of creatinine clearance vs. PENK in healthy subjects. Y axis: quartiles of Creatinine Clearance, x axis: quartiles of PENK.

FIG. 4: PENK highly correlated to creatinine clearance (r=−0.74, p<0,0001).

FIG. 5: Increased PENK was significantly correlated with kidney dysfunction.

FIG. 6: A receiver/operator curve (ROC) for Pro-Enkephalin and the diagnosis of Kidney Dysfunction according the RIFLE criteria (see above). The area under the curve (AUC) was 0.868, indicating a strong diagnostic power of Pro-Enkephalin for Kidney Dysfunction.

FIG. 7: Increased NGAL was significantly increased in patients with kidney dysfunction. The normal ranges of NGAL (range 0.037-0.106 µg/mL; http://www.bioporto.com/products/bioporto_diagnostics/ngal_elisa_kits/ngal_rapid_elisa_kit_ce_ivd) is indicated by a shadowed area in the graph.

FIG. 8: A receiver/operator curve (ROC) for NGAL and the diagnosis of Kidney Dysfunction according the RIFLE criteria (see above). We used NGAL as a reference marker for Kidney dysfunction. The AUC was 0,809, substantially lower than for Pro-Enkephalin (AUC 0.868, FIG. 6), indicating the incremental value of Pro-Enkephalin.

Figure 9:
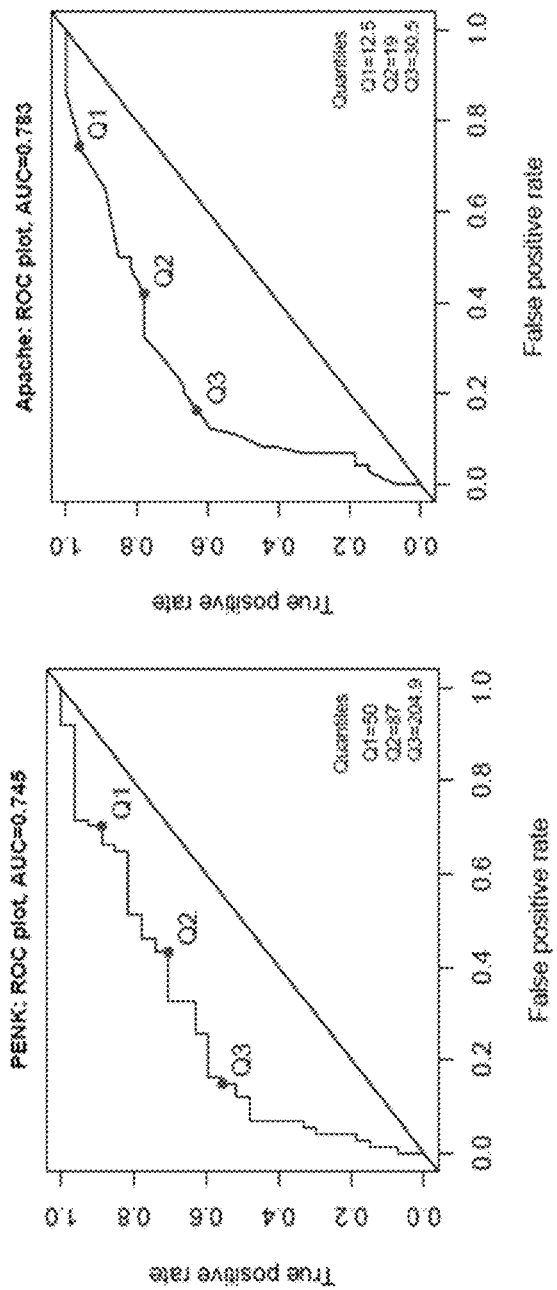

FIG. 9: PENK is highly prognostic for sepsis outcome

FIG. 10: There is a significant added information if PENK and APACHE 2 are combined FIG. 11a): A patient (survivor) with initial PENK<100 pmol/L and remained <100 pmol/L during hospital stay FIG. 11b): A patient (died during hospital stay) with initial PENK>100 pmol/L and was not reduced to values <100 pmol/L FIG. 11c): A patient (died during hospital stay) with initial PENK>100 pmol/L and was not reduced to values <100 pmol/L FIG. 11d): A patient (survivor) with initial PENK>100 pmol/L, the PENK value declined to values <100 pmol/L within one day of ICU treatment FIG. 12: PENK at first day (presentation at ED) was even stronger in prognosis of in hospital death in the male population FIG. 13: A combination of PENK and Apache resulted in an AUC of 0.89 vs. 0,837 Apache alone FIG. 14: The combination of PENK and creatinine clearance generated a superior prognostic value of AUC 0.91 vs. 0,721 for creatinine clearance alone FIG. 15: FIG. 15 A/B: Concentrations of plasma PENK (A) and NGAL (B), respectively, in septic patients categorized by grade of acute kidney dysfunction. 0=no kidney dysfunction; R=Risk; I=Injury; F=Failure; L=Loss. The categories are defined as follows (http://en.wikipedia.org/wiki/Acute_kidney_injury): Risk: GFR decrease >25%, serum creatinine increased 1.5 times or urine production of <0.5 ml/kg/hr for 6 hours; Injury: GFR decrease >50%, doubling of creatinine or urine production <0.5 ml/kg/hr for 12 hours; Failure: GFR decrease >75%, tripling of creatinine or creatinine >355 pmol/l (with a rise of >44) (>4 mg/dl) OR urine output below 0.3 ml/kg/hr for 24 hours; Loss: persistent AKI or complete loss of kidney function for more than 4 weeks. Normal ranges of PENK (see FIG. 2) and NGAL (range 0.037-0.106 µg/mL; http://www.bioporto.com/products/bioporto_diagnostics/ngal_elisa_kits/ngal_rapid_elisa_kit_ce_ivd) concentrations are indicated by shadowed areas in the graphs. The figure demonstrates that NGAL concentrations are massively elevated in septic patients even when they have no kidney dysfunction, whereas this is not the case for PENK.

Figure 16A:
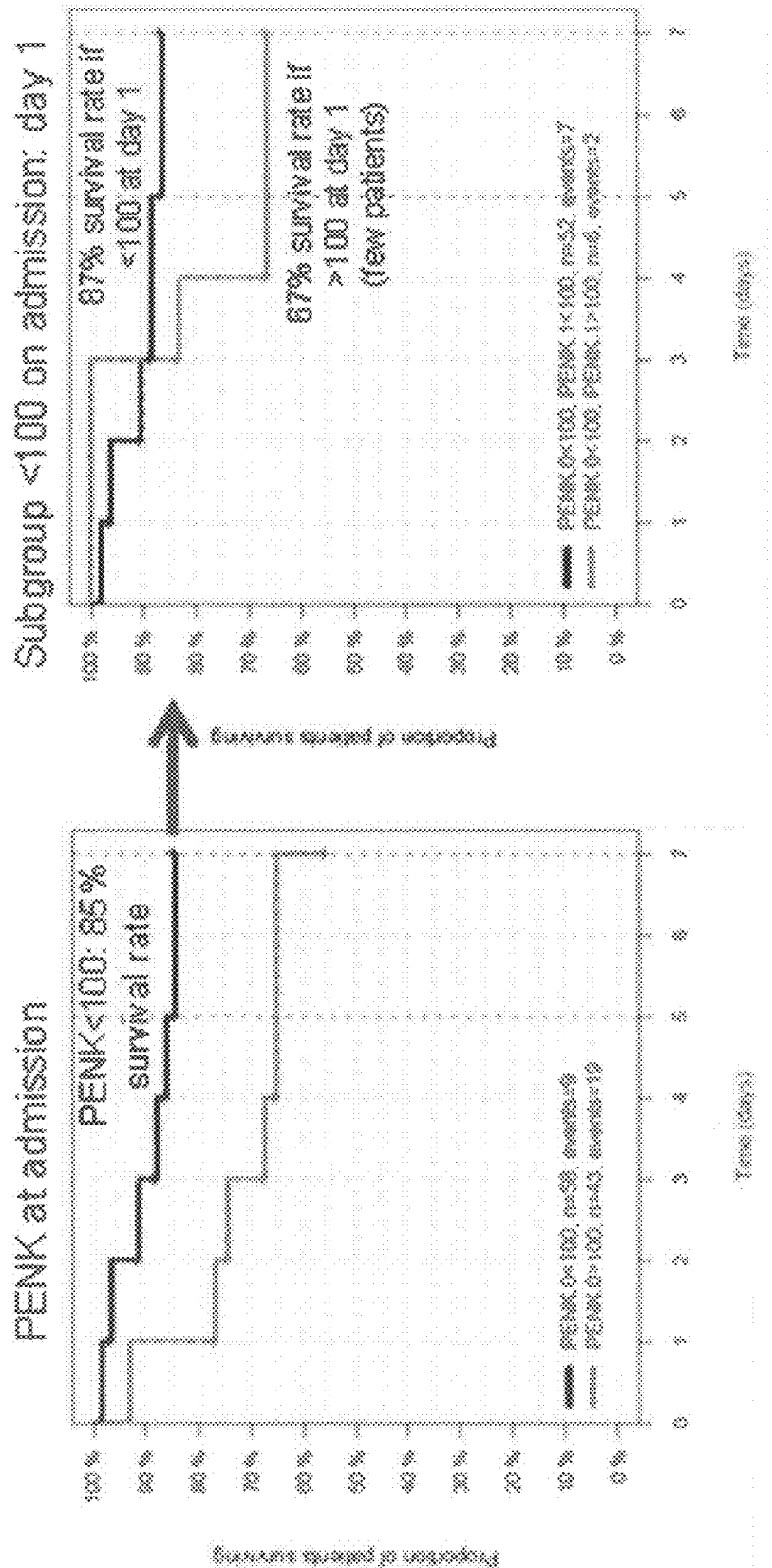
Figure 16B:
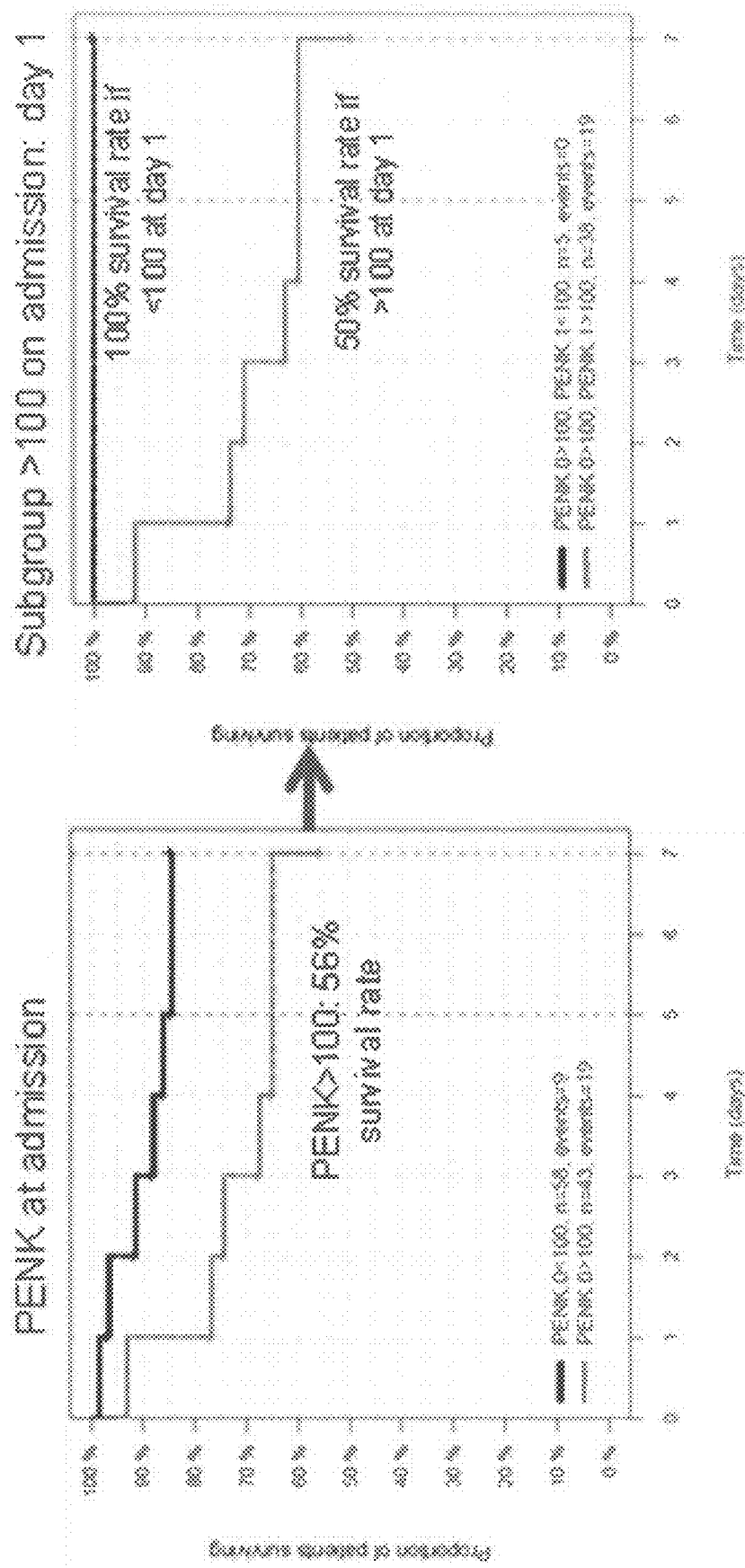
Figure 17:
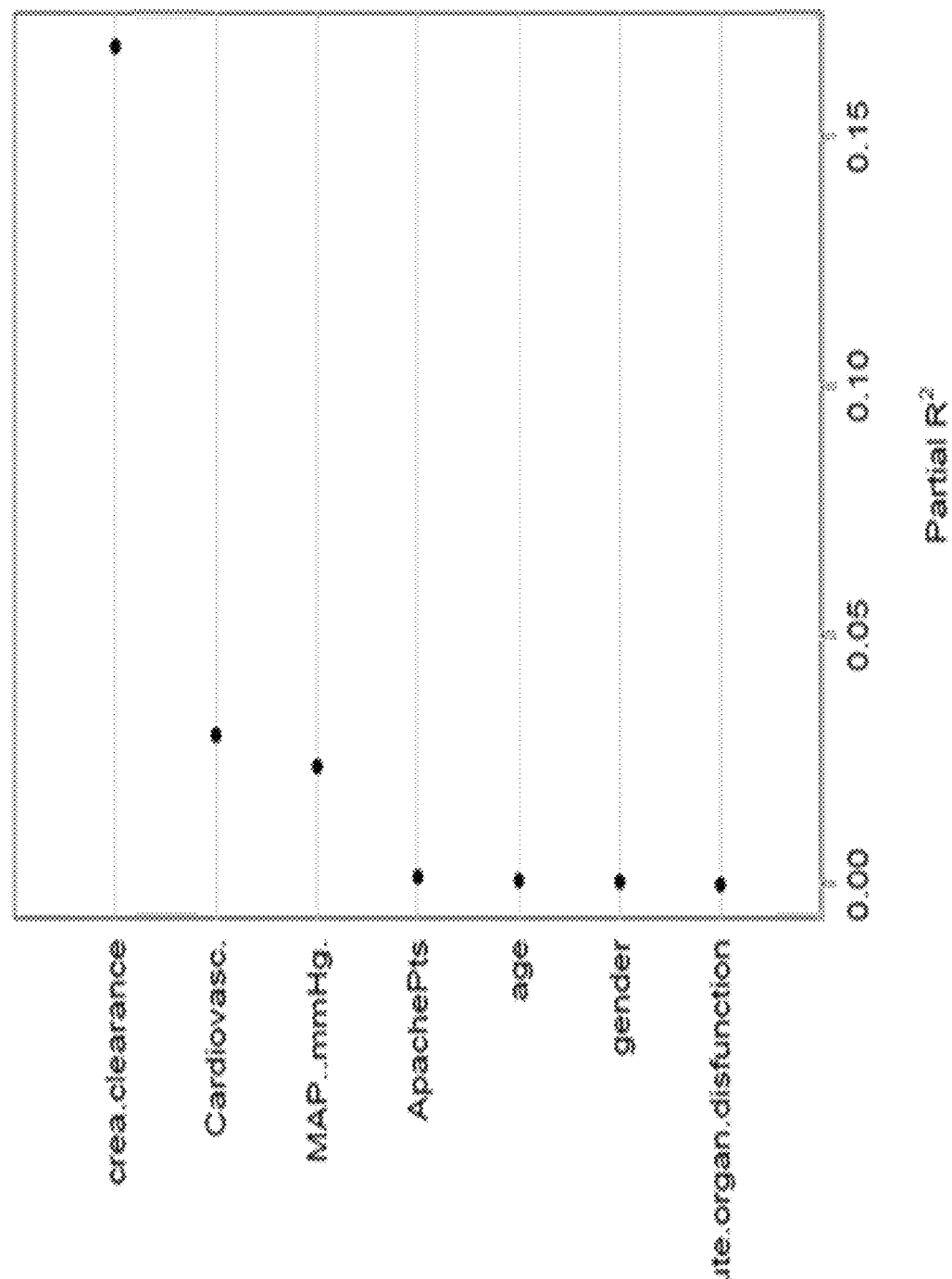

FIG. 16: Survival rates of critically ill patients depending on their plasma PENK concentrations on the day of admission and on the next day (day 1). Panel A: On the left hand side, the Kaplan-Meier-Plot is shown for those patient subpopulations with a PENK concentration on admission of above and below 100 pmol/L, respectively. On the right hand side the Kaplan-Meier-Plot is shown for those patient subpopulations with a PENK concentration on day 1 of above and below 100 pmol/L, respectively, who had a PENK concentration below 100 pmol/L on the day of admission. Panel B: On the left hand side, the Kaplan-Meier-Plot is shown for those patient subpopulations with a PENK concentration on admission of above and below 100 pmol/L, respectively. On the right hand side the Kaplan-Meier-Plot is shown for those patient subpopulations with a PENK concentration on day 1 of above and below 100 pmol/L, respectively, who had a PENK concentration above 100 pmol/L on the day of admission.

FIG. 17: Multivariable linear regression predicting PENK. Note: BP, Creatinine and Urea were left out due to high correlation with MAP or creatinine clearance. The linear regression was calculated using the variables listed as follows: Log(PENK)=a*CreaClearance+b*Cardiovasc+c*MAP+etc. Partial R2 gives the degree up to which each variable contributes to PENK, i.e. Crea Clearance is strongest and has a partial R2 of slightly above 0.15, i.e. crea clearance accounts for about 15% of the variability that you observe in PENK. Importantly, age, gender, etc. do not have a significant influence on PENK concentrations.

The invention claimed is:

1. A method comprising:

receiving a first sample comprising bodily fluid obtained from a subject and an antibody wherein said antibody has an amino acid sequence which is identical to an antibody produced by a process comprising:

fusing activated B-cells from a mammal previously immunized with a peptide comprising the sequence of Pro-Enkephalin or a fragment thereof, or with a conjugate of said peptide and a carrier protein, with cells of a myeloma cell line and culturing the resulting cells, screening said cultures of said fused cells and selecting IgG antibodies that bind to Pro-Enkephalin or a fragment thereof, and receiving a second sample of bodily fluid obtained from said subject and an antibody wherein said antibody has an amino acid sequence which is identical to an antibody produced by a process comprising:

fusing activated B-cells from a mammal previously immunized with a peptide comprising the sequence of Pro-Enkephalin or a fragment thereof, or with a conjugate of said peptide and a carrier protein, with cells of a myeloma cell line and culturing the resulting cells, screening said cultures of said fused cells and selecting IgG antibodies that bind to Pro-Enkephalin or a fragment thereof, and wherein the second sample is received after the first sample;

wherein the level of bound Pro-Enkephalin or fragments thereof of at least 5 amino acids in the first sample is lower than a level of Pro-Enkephalin or fragments thereof of at least 5 amino acids in the second sample, wherein said Pro-Enkephalin or fragment thereof is one or more of SEQ ID No. 1, SEQ ID No. 2, SEQ ID No. 5, SEQ ID No. 6, SEQ ID No. 8, SEQ ID No. 9, SEQ ID No. 10 or SEQ ID No. 11, the method additionally comprising treating the subject with a therapeutically effective amount of hyaluronic acid or renal replacement therapy.

2. A method according to claim 1, wherein the antibody binds to a region within the amino acid sequence SEQ ID No. 2, SEQ ID No. 5, SEQ ID No. 8, SEQ ID No. 9, SEQ ID No. 10 or SEQ ID No. 11 and does not bind to enkephalin peptides [Met]enkephalin SEQ ID No: 3, or [Leu]enkephalin SEQ ID No: 4.

3. A method according to claim 1, wherein the level of bound Pro-Enkephalin is measured with an immunoassay.

4. A method according to claim 1, wherein an assay is used for determining the level of bound Pro-Enkephalin or fragments thereof of at least 5 amino acids and wherein the assay sensitivity of said assay is able to quantify the Pro-Enkephalin or Pro-Enkephalin fragments of healthy subjects and is <15 pmol/L.

5. A method according to claim 1, wherein said bodily fluid is blood, serum, plasma, urine, cerebrospinal fluid (CSF), or saliva.

6. A method according to claim 1, additionally comprising measuring at least one clinical parameter is wherein said clinical parameter is blood urea nitrogen (BUN), neutrophil gelatinase-associated lipocalin (NGAL), Creatinine Clearance, Creatinine or Apache Score in each of said samples.

7. A method comprising:

receiving a first sample comprising bodily fluid obtained from a subject suffering from kidney dysfunction and an antibody wherein said antibody has an amino acid sequence which is identical to an antibody produced by a process comprising:

fusing activated B-cells from a mammal previously immunized with a peptide comprising the sequence of Pro-Enkephalin or a fragment thereof, or with a conjugate of said peptide and a carrier protein, with cells of a myeloma cell line and culturing the resulting cells, screening said cultures of said fused cells and selecting IgG antibodies that bind to Pro-Enkephalin or a fragment thereof, and receiving a second sample of bodily fluid obtained from said subject and a antibody wherein said antibody has an amino acid sequence which is identical to an antibody produced by a process comprising:

fusing activated B-cells from a mammal previously immunized with a peptide comprising the sequence of Pro-Enkephalin or a fragment thereof, or with a conjugate of said peptide and a carrier protein, with cells of a myeloma cell line and culturing the resulting cells, screening said cultures of said fused cells and selecting IgG antibodies that bind to Pro-Enkephalin or a fragment thereof, and wherein the second sample is received after the first sample;

wherein the level of bound Pro-Enkephalin or fragments thereof of at least 5 amino acids in the first sample is lower than a level of Pro-Enkephalin or fragments thereof of at least 5 amino acids in the second sample, wherein said Pro-Enkephalin or fragment thereof is one or more of SEQ ID No. 1, SEQ ID No. 2, SEQ ID No. 5, SEQ ID No. 6, SEQ ID No. 8, SEQ ID No. 9, SEQ ID No. 10 or SEQ ID No. 11.

8. The method of claim 7 wherein the subject has not been diagnosed with kidney dysfunction.

9. The method of claim 1 wherein the subject is an ICU patient.

10. The method of claim 1 wherein the subject has not suffered a stroke.

11. A method comprising:
receiving a sample comprising bodily fluid obtained from a subject suspected of suffering from kidney dysfunction and an antibody bound to Pro-Enkephalin or fragments thereof of at least 5 amino acids, wherein the amount of bound Pro-Enkephalin or fragments thereof of at least 5 amino acids to said binder is greater than 80 pmol MR-Pro-Enkephalin (MRPENK)/L, and wherein said antibody has an amino acid sequence which is identical to an antibody produced by a process comprising:

fusing activated B-cells from a mammal previously immunized with a peptide comprising the sequence of MR Pro-Enkephalin or a fragment thereof, or with a conjugate of said peptide and a carrier protein, with cells of a myeloma cell line and culturing the resulting cells, screening said cultures of said fused cells and selecting IgG antibodies that bind to Pro-Enkephalin or a fragment thereof.

12. The method according to claim 1, wherein the level of bound Pro-Enkephalin or one or more of said fragments thereof in the first sample is below a predetermined threshold, and wherein the level of bound Pro-Enkephalin or one or more of said fragments thereof in the second sample is above said threshold.

13. The method according to claim 12, wherein the threshold is 100 pmol/L.

14. The method according to claim 12, wherein the threshold is 80 pmol/l.

15. The method according to claim 12, wherein the threshold is 75 pmol/L.

16. The method according to claim 1, wherein the level of bound Pro-Enkephalin in the first sample is 100 pmol/L or higher and wherein the level of bound Pro-Enkephalin in the second sample is lower than in the first sample.

17. The method according to claim 1, wherein the level of bound Pro-Enkephalin in the first sample is 80 pmol/L or higher and wherein the level of bound Pro-Enkephalin in the second sample is lower than in the first sample.

18. The method according to claim 1, wherein the level of bound Pro-Enkephalin in the first sample is 75 pmol/L or higher and wherein the level of bound Pro-Enkephalin in the second sample is lower than in the first sample.

19. The method according to claim 16, wherein the subject suffers from a disease selected from sepsis, severe sepsis or septic shock.

20. The method according to claim 1, wherein the level of bound Pro-Enkephalin in the first sample is about 87 pmol/L or higher and wherein the level of bound Pro-Enkephalin in the second sample is lower than in the first sample.

21. The method according to claim 1, wherein the level of bound Pro-Enkephalin in the first sample is about 180 pmol/L or higher and wherein the level of bound Pro-Enkephalin in the second sample is lower than in the first sample.

22. The method according to claim 1, wherein the level of bound Pro-Enkephalin in the first sample is about 205 pmol/L or higher and wherein the level of bound Pro-Enkephalin in the second sample is lower than in the first sample.

23. The method according to claim 20, wherein the subject suffers from a disease selected from chronical kidney failure caused by immune responses to inflammation, acute kidney failure caused by decreased blood flow which may occur with extremely low blood pressure caused by trauma, traumatic patients, surgery, stroke, acute and chronic renal failure, patients with SIRS, Sepsis, Septic Shock, Stroke, acute- and post Myocardial Infarction, acute- and chronic Heart Failure, local and systemic bacterial and viral infections, autoimmune diseases, burned patients, cancer, liver diseases, lung diseases, patients receiving nephrotoxins such as cyclosporine, antibiotics including aminoglycosides and anticancer drugs such as cisplatin.

24. A method according to claim 1, wherein the antibody binds to a region within the amino acid sequence SEQ ID No. 1 or SEQ ID No. 6
and does not bind to enkephalin peptides [Met]enkephalin SEQ ID No: 3, or [Leu]enkephalin SEQ ID No: 4.

25. A method comprising:
receiving a sample comprising bodily fluid obtained from a subject suffering from kidney dysfunction and an antibody bound to Pro-Enkephalin or fragments thereof of at least 5 amino acids, wherein the amount of bound Pro-Enkephalin or fragments thereof of at least 5 amino acids to said antibody is greater than 80 pmol MR-Pro-Enkephalin (MRPENK)/L, and wherein said antibody has an amino acid sequence which is identical to an antibody produced by a process comprising:

fusing activated B-cells from a mammal previously immunized with a peptide comprising the sequence of Pro-Enkephalin or a fragment thereof, or with a conjugate of said peptide and a carrier protein, with cells of a myeloma cell line and culturing the resulting cells, screening said cultures of said fused cells and selecting IgG antibodies that bind to Pro-Enkephalin or a fragment thereof.

26. A method according to claim 25, wherein the level of bound Pro-Enkephalin is measured with an immunoassay.

27. A method according to claim 25, wherein an assay is used for determining the level of bound Pro-Enkephalin or fragments thereof of at least 5 amino acids and wherein the assay sensitivity of said assay is able to quantify the Pro-Enkephalin or Pro-Enkephalin fragments of healthy subjects and is <15 pmol/L.

28. A method according to claim 25, wherein said bodily fluid is blood, serum, plasma, urine, cerebrospinal fluid (CSF), or saliva.

29. A method according to claim 25, additionally comprising measuring at least one clinical parameter is wherein said clinical parameter is blood urea nitrogen (BUN), neutrophil gelatinase-associated lipocalin (NGAL), Creatinine Clearance, Creatinine or Apache Score in each of said samples.

30. The method of claim 25 wherein the subject is an ICU patient.

31. The method of claim 25 wherein the subject has not suffered a stroke.

32. The method according to claim 25, wherein the level of bound Pro-Enkephalin or one or more of said fragments thereof in the first sample is below a predetermined threshold, and wherein the level of bound Pro-Enkephalin or one or more of said fragments thereof in the second sample is above said threshold.

33. The method according to claim 25, wherein the level of bound Pro-Enkephalin in the first sample is 100 pmol/L or higher and wherein the level of bound Pro-Enkephalin in the second sample is lower than in the first sample.

34. The method according to claim 25, wherein the level of bound Pro-Enkephalin in the first sample is 80 pmol/L or higher and wherein the level of bound Pro-Enkephalin in the second sample is lower than in the first sample.

35. The method according to claim 25, wherein the level of bound Pro-Enkephalin in the first sample is 75 pmol/L or higher and wherein the level of bound Pro-Enkephalin in the second sample is lower than in the first sample.

36. The method according to claim 25, wherein the level of bound Pro-Enkephalin in the first sample is about 87 pmol/L or higher and wherein the level of bound Pro-Enkephalin in the second sample is lower than in the first sample.

37. The method according to claim 25, wherein the level of bound Pro-Enkephalin in the first sample is about 180 pmol/L or higher and wherein the level of bound Pro-Enkephalin in the second sample is lower than in the first sample.

38. The method according to claim 25, wherein the level of bound Pro-Enkephalin in the first sample is about 205 pmol/L or higher and wherein the level of bound Pro-Enkephalin in the second sample is lower than in the first sample.

39. A method according to claim 7, wherein the antibody binds to a region within the amino acid sequence SEQ ID No. 2, SEQ ID No. 5, SEQ ID No. 8, SEQ ID No. 9, SEQ ID No. 10 or SEQ ID No. 11,
and does not bind to enkephalin peptides [Met]enkephalin SEQ ID No: 3, or [Leu]enkephalin SEQ ID No: 4.

40. A method according to claim 7, wherein the level of bound Pro-Enkephalin is measured with an immunoassay.

41. A method according to claim 7, wherein an assay is used for determining the level of bound Pro-Enkephalin or fragments thereof of at least 5 amino acids and wherein the assay sensitivity of said assay is able to quantify the Pro-Enkephalin or Pro-Enkephalin fragments of healthy subjects and is <15 pmol/L.

42. A method according to claim 7, wherein said bodily fluid is blood, serum, plasma, urine, cerebrospinal fluid (CSF), or saliva.

43. A method according to claim 7, additionally comprising measuring at least one clinical parameter is wherein said clinical parameter is blood urea nitrogen (BUN), neutrophil gelatinase-associated lipocalin (NGAL), Creatinine Clearance, Creatinine or Apache Score in each of said samples.

44. The method of claim 7, wherein the subject is an ICU patient.

45. The method of claim 7, wherein the subject has not suffered a stroke.

46. The method according to claim 7, wherein the level of bound Pro-Enkephalin or one or more of said fragments thereof in the first sample is below a predetermined threshold, and wherein the level of bound Pro-Enkephalin or one or more of said fragments thereof in the second sample is above said threshold.

47. The method according to claim 7, wherein the level of bound Pro-Enkephalin in the first sample is 100 pmol/L or higher and wherein the level of bound Pro-Enkephalin in the second sample is lower than in the first sample.

48. The method according to claim 7, wherein the level of bound Pro-Enkephalin in the first sample is 80 pmol/L or higher and wherein the level of bound Pro-Enkephalin in the second sample is lower than in the first sample.

49. The method according to claim 7, wherein the level of bound Pro-Enkephalin in the first sample is 75 pmol/L or higher and wherein the level of bound Pro-Enkephalin in the second sample is lower than in the first sample.

50. The method according to claim 7, wherein the level of bound Pro-Enkephalin in the first sample is about 87 pmol/L or higher and wherein the level of bound Pro-Enkephalin in the second sample is lower than in the first sample.

51. The method according to claim 7, wherein the level of bound Pro-Enkephalin in the first sample is about 180 pmol/L or higher and wherein the level of bound Pro-Enkephalin in the second sample is lower than in the first sample.

52. The method according to claim 7, wherein the level of bound Pro-Enkephalin in the first sample is about 205 pmol/L or higher and wherein the level of bound Pro-Enkephalin in the second sample is lower than in the first sample.

53. The method of claim 1 wherein said peptide is selected from CDAEEDD, DAEEDD, CEEDDSLANSSDLLK, EEDDSLANSSDLLK, CLKELLETG, SEQ ID No. 13, CTGDNRERSHHQDGSDNE, TGDNRERSHHQDGSDNE, CSDNEEEVS, or SEQ ID No. 14.

54. The method of claim 7 wherein said peptide is selected from CDAEEDD, DAEEDD, CEEDDSLANSSDLLK, EEDDSLANSSDLLK, CLKELLETG, SEQ ID No. 13, CTGDNRERSHHQDGSDNE, TGDNRERSHHQDGSDNE, CSDNEEEVS, or SEQ ID No. 14.

55. The method of claim 1 wherein the Pro-Enkephalin or a fragment thereof is SEQ ID No. 6 (Mid-Regional Pro-Enkephalin).

56. The method of claim 7 wherein the Pro-Enkephalin or a fragment thereof is SEQ ID No. 6 (Mid-Regional Pro-Enkephalin).

57. The method of claim 25 wherein the Pro-Enkephalin or a fragment thereof is SEQ ID No. 6 (Mid-Regional Pro-Enkephalin).

\* \* \* \* \*

SEQUENCE LISTING

<160> NUMBER OF SEQ ID NOS: 24

<210> SEQ ID NO 1
<211> LENGTH: 243
<212> TYPE: PRT
<213> ORGANISM: Homo sapiens

<400> SEQUENCE: 1

Glu Cys Ser Gln Asp Cys Ala Thr Cys Ser Tyr Arg Leu Val Arg Pro
1               5                   10                  15

Ala Asp Ile Asn Phe Leu Ala Cys Val Met Glu Cys Glu Gly Lys Leu
            20                  25                  30

Pro Ser Leu Lys Ile Trp Glu Thr Cys Lys Glu Leu Leu Gln Leu Ser
        35                  40                  45

Lys Pro Glu Leu Pro Gln Asp Gly Thr Ser Thr Leu Arg Glu Asn Ser
50                  55                  60

Lys Pro Glu Glu Ser His Leu Leu Ala Lys Arg Tyr Gly Gly Phe Met
65                  70                  75                  80

Lys Arg Tyr Gly Gly Phe Met Lys Lys Met Asp Glu Leu Tyr Pro Met
                85                  90                  95

Glu Pro Glu Glu Glu Ala Asn Gly Ser Glu Ile Leu Ala Lys Arg Tyr
            100                 105                 110

Gly Gly Phe Met Lys Lys Asp Ala Glu Glu Asp Ser Leu Ala Asn
            115                 120                 125

Ser Ser Asp Leu Leu Lys Glu Leu Leu Glu Thr Gly Asp Asn Arg Glu
130                 135                 140

Arg Ser His His Gln Asp Gly Ser Asp Asn Glu Glu Glu Val Ser Lys
145                 150                 155                 160

Arg Tyr Gly Gly Phe Met Arg Gly Leu Lys Arg Ser Pro Gln Leu Glu
                165                 170                 175

Asp Glu Ala Lys Glu Leu Gln Lys Arg Tyr Gly Gly Phe Met Arg Arg
            180                 185                 190

Val Gly Arg Pro Glu Trp Trp Met Asp Tyr Gln Lys Arg Tyr Gly Gly
        195                 200                 205

Phe Leu Lys Arg Phe Ala Glu Ala Leu Pro Ser Asp Glu Glu Gly Glu
    210                 215                 220

Ser Tyr Ser Lys Glu Val Pro Glu Met Glu Lys Arg Tyr Gly Gly Phe
225                 230                 235                 240

Met Arg Phe

<210> SEQ ID NO 2
<211> LENGTH: 73
<212> TYPE: PRT
<213> ORGANISM: Homo sapiens

<400> SEQUENCE: 2

Glu Cys Ser Gln Asp Cys Ala Thr Cys Ser Tyr Arg Leu Val Arg Pro
1               5                   10                  15

Ala Asp Ile Asn Phe Leu Ala Cys Val Met Glu Cys Glu Gly Lys Leu
            20                  25                  30

Pro Ser Leu Lys Ile Trp Glu Thr Cys Lys Glu Leu Leu Gln Leu Ser
        35                  40                  45

Lys Pro Glu Leu Pro Gln Asp Gly Thr Ser Thr Leu Arg Glu Asn Ser
50                  55                  60

Lys Pro Glu Glu Ser His Leu Leu Ala
65                  70

```
<210> SEQ ID NO 3
<211> LENGTH: 5
<212> TYPE: PRT
<213> ORGANISM: Homo sapiens

<400> SEQUENCE: 3

Tyr Gly Gly Phe Met
1               5

<210> SEQ ID NO 4
<211> LENGTH: 5
<212> TYPE: PRT
<213> ORGANISM: Homo sapiens

<400> SEQUENCE: 4

Tyr Gly Gly Phe Leu
1               5

<210> SEQ ID NO 5
<211> LENGTH: 20
<212> TYPE: PRT
<213> ORGANISM: Homo sapiens

<400> SEQUENCE: 5

Met Asp Glu Leu Tyr Pro Met Glu Pro Glu Glu Glu Ala Asn Gly Ser
1               5                   10                  15

Glu Ile Leu Ala
            20

<210> SEQ ID NO 6
<211> LENGTH: 41
<212> TYPE: PRT
<213> ORGANISM: Homo sapiens

<400> SEQUENCE: 6

Asp Ala Glu Glu Asp Asp Ser Leu Ala Asn Ser Ser Asp Leu Leu Lys
1               5                   10                  15

Glu Leu Leu Glu Thr Gly Asp Asn Arg Glu Arg Ser His His Gln Asp
            20                  25                  30

Gly Ser Asp Asn Glu Glu Glu Val Ser
        35                  40

<210> SEQ ID NO 7
<211> LENGTH: 8
<212> TYPE: PRT
<213> ORGANISM: Homo sapiens

<400> SEQUENCE: 7

Tyr Gly Gly Phe Met Arg Gly Leu
1               5

<210> SEQ ID NO 8
<211> LENGTH: 12
<212> TYPE: PRT
<213> ORGANISM: Homo sapiens

<400> SEQUENCE: 8

Ser Pro Gln Leu Glu Asp Glu Ala Lys Glu Leu Gln
1               5                   10

<210> SEQ ID NO 9
<211> LENGTH: 11
```

<212> TYPE: PRT
<213> ORGANISM: Homo sapiens

<400> SEQUENCE: 9

Val Gly Arg Pro Glu Trp Trp Met Asp Tyr Gln
1               5                   10

<210> SEQ ID NO 10
<211> LENGTH: 22
<212> TYPE: PRT
<213> ORGANISM: Homo sapiens

<400> SEQUENCE: 10

Phe Ala Glu Ala Leu Pro Ser Asp Glu Glu Gly Glu Ser Tyr Ser Lys
1               5                   10                  15

Glu Val Pro Glu Met Glu
            20

<210> SEQ ID NO 11
<211> LENGTH: 29
<212> TYPE: PRT
<213> ORGANISM: Homo sapiens

<400> SEQUENCE: 11

Phe Ala Glu Ala Leu Pro Ser Asp Glu Glu Gly Glu Ser Tyr Ser Lys
1               5                   10                  15

Glu Val Pro Glu Met Glu Lys Arg Tyr Gly Gly Phe Met
            20                  25

<210> SEQ ID NO 12
<211> LENGTH: 7
<212> TYPE: PRT
<213> ORGANISM: Homo sapiens

<400> SEQUENCE: 12

Tyr Gly Gly Phe Met Arg Phe
1               5

<210> SEQ ID NO 13
<211> LENGTH: 8
<212> TYPE: PRT
<213> ORGANISM: Homo sapiens

<400> SEQUENCE: 13

Leu Lys Glu Leu Leu Glu Thr Gly
1               5

<210> SEQ ID NO 14
<211> LENGTH: 8
<212> TYPE: PRT
<213> ORGANISM: Homo sapiens

<400> SEQUENCE: 14

Ser Asp Asn Glu Glu Glu Val Ser
1               5

<210> SEQ ID NO 15
<211> LENGTH: 6
<212> TYPE: PRT
<213> ORGANISM: Homo sapiens

<400> SEQUENCE: 15

Asp Ala Glu Glu Asp Asp
1               5

```
<210> SEQ ID NO 16
<211> LENGTH: 14
<212> TYPE: PRT
<213> ORGANISM: Homo sapiens

<400> SEQUENCE: 16

Glu Glu Asp Asp Ser Leu Ala Asn Ser Ser Asp Leu Leu Lys
1               5                  10

<210> SEQ ID NO 17
<211> LENGTH: 8
<212> TYPE: PRT
<213> ORGANISM: Homo sapiens

<400> SEQUENCE: 17

Leu Lys Glu Leu Leu Glu Thr Gly
1               5

<210> SEQ ID NO 18
<211> LENGTH: 17
<212> TYPE: PRT
<213> ORGANISM: Homo sapiens

<400> SEQUENCE: 18

Thr Gly Asp Asn Arg Glu Arg Ser His His Gln Asp Gly Ser Asp Asn
1               5                  10                 15

Glu

<210> SEQ ID NO 19
<211> LENGTH: 8
<212> TYPE: PRT
<213> ORGANISM: Homo sapiens

<400> SEQUENCE: 19

Ser Asp Asn Glu Glu Glu Val Ser
1               5

<210> SEQ ID NO 20
<211> LENGTH: 7
<212> TYPE: PRT
<213> ORGANISM: Artificial Sequence
<220> FEATURE:
<223> OTHER INFORMATION: Immunization Peptide with added Cys

<400> SEQUENCE: 20

Cys Asp Ala Glu Glu Asp Asp
1               5

<210> SEQ ID NO 21
<211> LENGTH: 15
<212> TYPE: PRT
<213> ORGANISM: Artificial Sequence
<220> FEATURE:
<223> OTHER INFORMATION: Immunization Peptide with added Cys

<400> SEQUENCE: 21

Cys Glu Glu Asp Asp Ser Leu Ala Asn Ser Ser Asp Leu Leu Lys
1               5                  10                 15

<210> SEQ ID NO 22
<211> LENGTH: 9
<212> TYPE: PRT
<213> ORGANISM: Artificial Sequence
<220> FEATURE:
```

```
<223> OTHER INFORMATION: Immunization Peptide with added Cys

<400> SEQUENCE: 22

Cys Leu Lys Glu Leu Leu Glu Thr Gly
1               5

<210> SEQ ID NO 23
<211> LENGTH: 18
<212> TYPE: PRT
<213> ORGANISM: Artificial Sequence
<220> FEATURE:
<223> OTHER INFORMATION: Immunization Peptide with added Cys

<400> SEQUENCE: 23

Cys Thr Gly Asp Asn Arg Glu Arg Ser His His Gln Asp Gly Ser Asp
1               5                   10                  15

Asn Glu

<210> SEQ ID NO 24
<211> LENGTH: 9
<212> TYPE: PRT
<213> ORGANISM: Artificial Sequence
<220> FEATURE:
<223> OTHER INFORMATION: Immunization Peptide with added Cys

<400> SEQUENCE: 24

Cys Ser Asp Asn Glu Glu Glu Val Ser
1               5
```